US009915592B2

(12) United States Patent
Sood et al.

(10) Patent No.: US 9,915,592 B2
(45) Date of Patent: Mar. 13, 2018

(54) METHODS OF ANALYZING AN H AND E STAINED BIOLOGICAL SAMPLE

(71) Applicant: General Electric Company, Schenectady, NY (US)

(72) Inventors: Anup Sood, Clifton Park, NY (US); Kevin Bernard Kenny, Niskayuna, NY (US); Arunkumar Natarajan, Niskayuna, NY (US); Lakshmi Sireesha Kaanumalle, Niskayuna, NY (US); Elizabeth Mary McDonough, Niskayuna, NY (US)

(73) Assignee: General Electric Company, Schenectady, NY (US)

(*) Notice: Subject to any disclaimer, the term of this patent is extended or adjusted under 35 U.S.C. 154(b) by 271 days.

(21) Appl. No.: 14/772,305

(22) PCT Filed: Mar. 5, 2014

(86) PCT No.: PCT/US2014/020659
§ 371 (c)(1),
(2) Date: Sep. 2, 2015

(87) PCT Pub. No.: WO2014/138197
PCT Pub. Date: Sep. 12, 2014

(65) Prior Publication Data
US 2016/0069782 A1 Mar. 10, 2016

Related U.S. Application Data

(63) Continuation of application No. 13/786,747, filed on Mar. 6, 2013, now Pat. No. 9,176,032.

(51) Int. Cl.
*G01N 1/30* (2006.01)
*G01N 33/50* (2006.01)
*G01N 33/58* (2006.01)

(52) U.S. Cl.
CPC .......... *G01N 1/30* (2013.01); *G01N 33/5005* (2013.01); *G01N 33/582* (2013.01)

(58) Field of Classification Search
None
See application file for complete search history.

(56) References Cited

U.S. PATENT DOCUMENTS 4,524,014 A 6/1985 Finch et al.
5,648,227 A 7/1997 Basboll
(Continued)

FOREIGN PATENT DOCUMENTS

CN 1479870 A 3/2004
EP 1234026 B1 8/2011
(Continued)

OTHER PUBLICATIONS

Yoon et al, Healthcare Informatics Res., vol. 22, pp. 238-242, Jul. 2016.*
(Continued)

*Primary Examiner* — Robert T. Crow
(74) *Attorney, Agent, or Firm* — Eversheds Sutherland (US) LLP

(57) ABSTRACT

Methods comprising probing multiple targets in an H&E stained biological sample are provided. The methods include the steps of providing a hematoxylin and eosin stained biological sample containing multiple targets, optionally detecting H&E staining of the sample, removing the hematoxylin and eosin signals, and detecting additional features or targets in the biological sample. The detecting step may include performing the steps of binding at least one probe to one or more targets to the sample, detecting a signal from the probe and contacting the sample with a bleaching agent. The process of binding, detecting and bleaching may be iteratively repeated.

30 Claims, 15 Drawing Sheets

(56) References Cited

U.S. PATENT DOCUMENTS

| | | | |
|---|---|---|---|
| 6,451,551 | B1 | 9/2002 | Zhan et al. |
| 6,627,177 | B2 | 9/2003 | Singaram et al. |
| 6,804,544 | B2 | 10/2004 | Van Antwerp et al. |
| 6,924,115 | B2 | 8/2005 | Schubert |
| 7,045,361 | B2 | 5/2006 | Heiss et al. |
| 7,329,505 | B2 | 2/2008 | Marme |
| 7,629,125 | B2 | 12/2009 | Sood et al. |
| 7,714,303 | B2 | 5/2010 | Lundquist et al. |
| 7,741,045 | B2 | 6/2010 | Gerdes et al. |
| 7,741,046 | B2 | 6/2010 | Larsen et al. |
| 7,803,634 | B2 | 9/2010 | Klimov et al. |
| 7,919,254 | B2 | 4/2011 | Cohen et al. |
| 7,993,927 | B2 | 8/2011 | Frangioni |
| 8,036,462 | B2 | 10/2011 | Can et al. |
| 8,060,348 | B2 | 11/2011 | Cline et al. |
| 8,062,897 | B2 | 11/2011 | Capodieci et al. |
| 8,131,476 | B2 | 3/2012 | Cline et al. |
| 9,176,032 | B2 * | 11/2015 | Sood .................. G01N 1/30 |
| 2002/0043651 | A1 | 4/2002 | Darrow et al. |
| 2002/0081612 | A1 * | 6/2002 | Katz .................. C12Q 1/6886 435/6.14 |
| 2004/0146990 | A1 * | 7/2004 | Mather ............... C07K 14/705 435/70.21 |
| 2006/0083688 | A1 | 4/2006 | Singram et al. |
| 2008/0032321 | A1 | 2/2008 | Ginty et al. |
| 2008/0118944 | A1 | 5/2008 | Larsen et al. |
| 2009/0263612 | A1 | 10/2009 | Gascoyne et al. |
| 2010/0120043 | A1 | 5/2010 | Sood et al. |
| 2010/0216652 | A1 | 8/2010 | Eberwine et al. |
| 2011/0092381 | A1 | 4/2011 | Sood et al. |
| 2012/0112098 | A1 | 5/2012 | Hoyt |
| 2014/0024024 | A1 | 1/2014 | Sood et al. |

FOREIGN PATENT DOCUMENTS

| | | | |
|---|---|---|---|
| WO | 2006132710 | A1 | 12/2006 |
| WO | 2007136724 | A2 | 11/2007 |
| WO | 2008052338 | A1 | 5/2008 |
| WO | 2008133729 | A2 | 11/2008 |
| WO | 2011048184 | A1 | 4/2011 |

OTHER PUBLICATIONS

Lev et al, Histochemie, vol. 20, pp. 363-377, 1969.*
Thermo Scientific 2009.*
Thermo Scientific 2008.*
Mittag et al, Cytometry Part A 69A, pp. 139-141 (2006).*
Larson et al, Dermat. Surg., vol. 37, pp. 1089-1099 (2011).*
Miller et al., "Photopolymerization Studies. III. Thermal Sensitization and Desensitization Effects", Macromolecules, vol. No. 7, Issue No. 2, pp. 179-187, 1974.
Eaton, "Dye-Sensitized Photopolymerization: Activation by Trialkylbenzylstannanes", Photographic Science and Engineering, vol. No. 23, pp. 150-154, 1979.
Eaton, "Electron Transfer Induced Photofragmentation as a Route to Free Radicals", Pure and Applied Chemistry, vol. No. 56, Issue No. 9, pp. 1191-1202, 1984.
Eaton, "Electron Transfer Processes in Imaging", Topics in Current Chemistry, vol. No. 156, pp. 199-225, 1990.
Borduchi et al., "A Simple Procedure for Rehybridization of Nuclei Analyzed Previously by Fish", Genetics and Molecular Biology, vol. No. 22, Issue No. 2, pp. 173-175, 1999.
Toth et al., "Simultaneous Visualization of Multiple Antigens with Tyramide Signal Amplification using Antibodies from the same Species", Journal of Histochemistry & Cytochemistry, vol. No. 55, Issue No. 6, pp. 545-554, 2007.
Zrazhevskiy et al., "Quantum Dot Imaging Platform for Single-Cell Molecular Profiling", Nature Communications, vol. No. 4, 2013.
Chinese Office Action issued in connection with corresponding Application No. 201280070449.4 dated Jun. 24, 2015.
European Search Report and Written Opinion issued from EP Application No. 1286015938 dated Apr. 8, 2015.
Pulcment/Excalibur: "If combined with hematoxylin eosin staining," Aug. 27, 2009, XP002725399, retrieved from the internet: http://www.ihcworld.corn/smf/index.php?topic=3028.0, 2 pages.
International Search Report and Written Opinion from PCT Application No. PCT/US2012/067527 dated Feb. 8, 2013.
Benharroch et al., "ALK-Positive Lymphoma: A Single Disease with a Broad Spectrum of Morphology," Blood—Journal of the American Society of Hematology, vol. 91, Issue 6, Mar. 15, 1998, pp. 2076-2084.
International Search Report and Written Opinion from PCT Application No. PCT/US2014/020659 dated Jun. 30, 2014, 11 pages.
Walgenbach-Bruenagel G., et al., "Detection of lymphatic invasion in early stage primary colorectal cancer with the monoclonal antibody D2-40," European Surgical Research, vol. 28, Aug. 15, 2006, pp. 438-444.
Helin H.O., et al., "Virtual Microschopy in Prostate Histopathology: Simultaneous Viewing of Biopsies Stained Sequentially with Hematoxylin and Eosin, and alpha-Methylacyl-Coenzyme A racemase/p63 Immunohistochemistry," Journal of Urology, Baltimore MD, Feb. 1, 2006, vol. 175, No. 2, pp. 495-499.
Tehmina, AZ, et al., "False positive labeling of prostate cancer with high molecular weight cyrokeratin: p63 a more specific immunomarker for basal cells," American Journal of Surgical Pathology, vol. 32, No. 12, Dec. 1, 2008, pp. 1890-1895.
Dardik, Michael et al., "Efficacy of restaining prostate needle biopsies with high-molecular weigh cytokertin," Human Pathology, vol. 31, No. 9, Sep. 1, 2000, pp. 115-1161.
Chen M., "Evaluation of applying Feulgen stain for DNA analysis on destained hematoxylin-eosin-stained cytologic smears," Analytical and Quantitative Cytology and Histology, vol. 26, No. 5, Oct. 1, 2004, pp. 255-258.
Chatterjee et al. "Photochemistry of Carbocyanine Alkyltriphenylborate Salts: Intro-Ion-Pair Electron Transfer and the Chemistry of Boranyl Radicals." J. Am. Chem. Society, No. 112, No. 17, pp. 6329-6338, 1990.
Paczowski et al., "Polymethine Dyes as Fluorescent Probes and Visible-Light Photoinitiators for Free Radical Polymerization," Topics in Heterocyclic Chemistry, vol. 14, pp. 183-220, 2008.
Co-pending U.S. Appl. No. 13/551,190, filed Dec. 23, 2011, entitled "Methods of Detecting DNA, RNA and Protein in Biological Samples."

* cited by examiner

H & E Slide-
Brightfield

↓ AR

H & E Slide-
Brightfield

↕

Residual
Eosin
Fluorescence

Residual Eosin Fluorescence

↓ PICB

Autofluorescence after PICB

Control slide - No H & E

METHODS OF ANALYZING AN H AND E STAINED BIOLOGICAL SAMPLE

This application is a filing under 35 U.S.C. 371 of international application number PCT/US2014/020659, filed Mar. 5, 2014, which claims priority to U.S. application Ser. No. 13/786,747, filed Mar. 6, 2013, the entire disclosures of each of which are hereby incorporated by reference.

BACKGROUND

Traditionally, hematoxylin and eosin staining (H&E) is one of the most common staining methods in histology. The morphology from the H&E is most widely used in medical diagnosis for cancer detection. However, increasingly molecular analysis of tissue by immunohistochemistry (IHC) or immunofluorescence (IF) and fluorescence in situ hybridization have become an essential part of cancer diagnosis in addition to morphological assessment. With great strides in targeted therapies, detailed molecular assessment of cancer tissue is fast becoming a requirement. Additionally with early cancer detection sample size is diminishing, making it difficult to perform various analyses required for complete characterization of disease.

While valuable, many of these current techniques may detect only a few targets at one time (such as IHC or fluorescence-based Western blots where number of targets detectable is limited by the fluorescence-based detection system) in a single sample. Further analysis of targets may require use of additional biological samples from the source, limiting the ability to determine relative characteristics of the targets such as the presence, absence, concentration, and/or the spatial distribution of multiple biological targets in the biological sample. Moreover, in certain instances, a limited amount of sample may be available for analysis or the individual sample may require further analysis.

Furthermore in many older cases only samples available are H&E stained slides and as patients are relapsing molecular analysis of this tissue can significantly benefit these patients by matching their disease to available targeted therapies. A major problem with using the previously H&E stained slide for IHC and FISH is the interference from H&E stains in both chromogenic detection in IHC and fluorescence detection for IF and FISH. Attempts have been made to remove H&E from tissue for interrogation. While this has allowed IHC with chromogen detection, IF and FISH are not feasible due to strong residual fluorescence from eosin. Removal of residual eosin fluorescence has not been feasible with many different techniques attempted to date.

For this reason, the general practice has been to use different tissue sections for H&E and molecular analysis. In rare cases where previously stained H&E slides are the only sample available, partial removal of H&E is performed and the slides are used for IHC using a chromogenic signal (Benharroch et. al. Blood 1998, 91:2076-2084). In limited circumstances it may also be possible to perform IF or FISH using a fluorophore whose emission is far removed from the eosin fluorescence, however, most of the commercial probes or labeled antibodies are labeled with fluorophores whose emission overlaps with eosin emission.

Thus there still remains a need for a method to remove H &E signals from the tissue and use the same tissue section for subsequent analysis such as immunofluorescence and FISH.

BRIEF DESCRIPTION

Disclosed herein are novel methods for probing multiple targets in a hematoxylin and eosin stained biological sample. In some embodiments, a method of probing multiple targets in a biological sample comprising a number of steps is disclosed. The steps include optionally detecting the hematoxylin and eosin staining of the biological sample containing multiple targets; removing fluorescent H&E signal from the hematoxylin and eosin stained biological sample; and detecting additional features or targets in the biological sample. Additional features may include any morphological feature, e.g. mucins, fat, connective tissue, amyloid, myelin, etc. that may be detected by a different staining method other than an H&E stain.

In certain embodiments, the hematoxylin and eosin staining uses an eosin Y analog which has a low fluorescence and the removing step includes a wash using a buffered aqueous solution or a series of washes with solvents and buffers depending upon the desired amount of reduction in eosin signal. Eosin analogs with a low fluorescence may include, for example, eosin-B, phloxin B or erythrosin.

In certain embodiments, the removal of fluorescent H&E signal is accomplished by
(i) washing the sample using a buffered aqueous solution to remove the hematoxylin and partially remove the eosin;
(ii) contacting the sample with a charge transfer agent to quench the eosin fluorescence; and
(iii) optionally washing the sample using a buffered aqueous solution. Quaternary ammonium salts charge transfer reagent may be selected from, for example, Methyl Viologen (p-Quat), diquat and phenylene diamine dihydrochloride salts.

In certain embodiments, the removal of fluorescent H&E signal is accomplished by washing the sample using a buffered aqueous solution to remove the hematoxylin and partially remove the eosin; and contacting the sample with hydroxyl radicals generated in situ. In certain embodiments hydroxyl radicals are generated in situ by applying hydrogen peroxide and a metal salt. In certain other embodiments, it further comprises irradiation the sample with light.

In certain embodiments, the removal of fluorescent H&E signal is accomplished by
(i) washing the sample using a buffered aqueous solution to remove the hematoxylin and partially remove the eosin;
(ii) contacting the sample with an electron transfer reagent; and
(iii) irradiating the sample to remove residual fluorescence. In certain embodiments, irradiating the sample is accomplished by exposing the sample to light of 350 nm-1.3 µM in wavelength. In certain preferred embodiments, irradiating the sample is accomplished by exposing the sample to light of 400-700 nm in wavelength. In certain other embodiments, the eosin is irreversibly modified. In still other embodiments, no detectable fluorescent signal from Eosin is detected after sample irradiation.

In some embodiments, the electron transfer reagent (photo-induced chemical bleaching (PICB) agent) is a borate salt. In some embodiments, the borate salt is represented by the following structural formula:

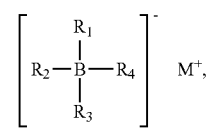

wherein:
each $R_1$, $R_2$, and $R_3$ is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro.

$R_4$ is an alkyl, an alkenyl, or an akynyl, wherein said alkyl, alkenyl, or alkynyl is optionally substituted with one or more substituents selected from the group consisting of (C1-C4)alkyl, aryl, (C1-C4)alkoxy, (C1-C4) alkylamino, amino, hydroxyl, cyano, halogen, or nitro, and $M^+$ is selected from the group consisting of organic and inorganic cations.

In still other embodiments, the detecting step for additional features or targets in the biological sample includes detecting additional targets in the sample. Thus the detecting step of the method comprises the additional steps of binding at least one probe to one or more targets of the sample, detecting a signal from the probe bound, and optionally removing the signal and repeating the binding, detecting and optional removing steps.

The signal removal step may comprise contacting the sample with a bleaching or stripping agent or subjected the sample to heat to remove the probe or probe signal. In certain embodiments, the stripping agent is SDS and the probe is an antibody. In certain other embodiments, the probe is stripped by direct heat or microwave induced heat in the presence of a buffer.

The bleaching agent may be a photoactivated chemical bleaching agent and the sample contacted with the bleaching agent is further irradiated by exposing the sample to light of 350 nm-1.3 µM in wavelength. In certain embodiments, irradiating the sample is accomplished by exposing the sample to light of 400-700 nm in wavelength. In certain other embodiments, the at least one probe comprises a fluorescent signal generator, and the signal detected is a fluorescent signal. In still other embodiments, the method further comprises measuring one or more intensity values of the signal detected in the detecting step. In other embodiments, the intensity values are correlated with an amount of target present in the sample.

In still other embodiments, the eosin Y signal may be quenched by adding a charge transfer reagent to the sample, before the signal detecting step, to quench residual fluorescence.

In certain embodiments, the removal of fluorescent signal from the H&E staining includes adding a charge transfer reagent to the sample, before detecting signals from the probe, to quench residual eosin fluorescence.

In still other embodiments, the binding, detecting and optional contacting steps are repeated two or more times.

In certain embodiments, the invention provides a method of probing multiple targets in a hematoxylin and eosin stained biological sample, comprising:
(a) optionally detecting the hematoxylin and eosin staining of the biological sample containing multiple targets;
(b) optionally removing the hematoxylin and partially removing the eosin by washing the sample;
(c) subjecting the sample to an antigen retrieval process to expose one or more antigens in the region of interest;
(d) optionally applying a blocking reagent to block against nonspecific binding of one or more probes;
(e) removing fluorescent signals from the hematoxylin and eosin stained biological sample;
(f) binding at least one probe to one or more targets present in the sample;
(g) detecting a signal from the probe bound; and
(h) optionally removing the signal and repeating steps (f) through (h).

In certain embodiments, the probe is a protein binder.

In certain other embodiments, the signal removal in step (h) comprises contacting the sample with a bleaching agent or stripping agent or subjecting the sample to heat to remove the probe or probe signal. For example, signal removal may be achieved by denaturing the probe with heat, microwave generated heat or a detergent, e.g. SDS. Signal removal may also be achieved using a bleaching agent, such as a photoactivated chemical bleaching agent and the signal removal step further comprises irradiating the sample by exposing the sample to light of 350 nm-1.3 µM in wavelength.

In certain other embodiments, an electron transfer agent is used for both steps (e) and (h) for signal removal and these steps further comprises irradiating the sample by exposing the sample to light of 350 nm-1.3 µM in wavelength.

In certain embodiments, the invention provides a method of probing multiple targets in a hematoxylin and eosin stained biological sample, comprising:
(a) optionally detecting the hematoxylin and eosin staining in the biological sample containing multiple targets;
(b) removing fluorescent signals from the hematoxylin and eosin stained biological sample;
(c) binding at least one probe to one or more targets present in the sample;
(d) detecting a signal from the probe bound; and
(e) optionally removing the signal and repeating steps (c) through (e).

In certain embodiments, the signal removal in step (e) comprises subjecting the sample to a bleaching agent, protein denaturant, DNA denaturant, heat, SDS or a combination thereof.

In certain other embodiments, the at least one probe is a FISH probe.

DETAILED DESCRIPTION

Figure 1:
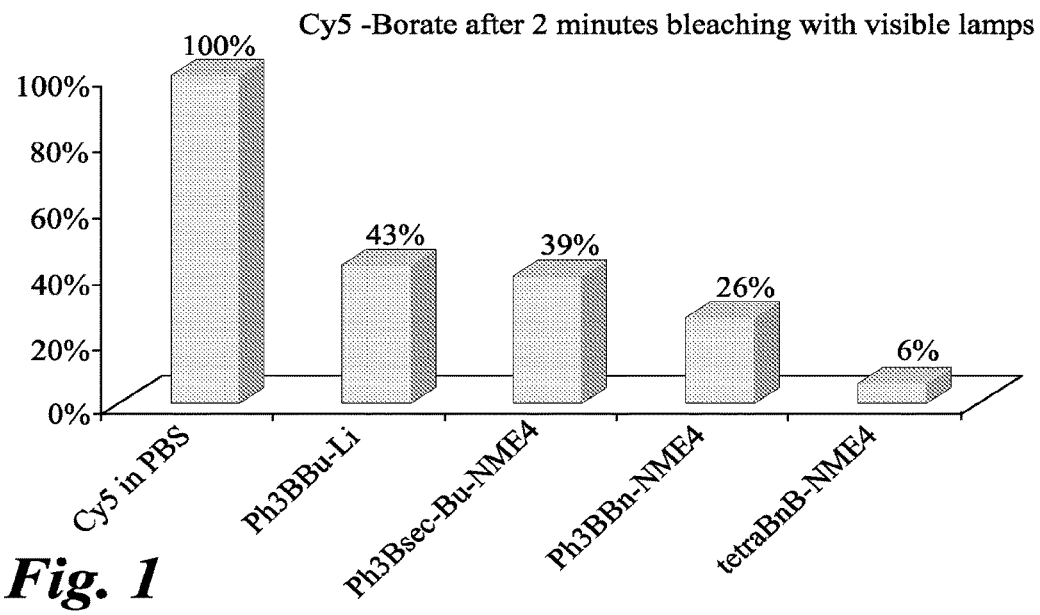
FIG. 1 is a standardized graph showing the percentage of signal intensity, compared to a control sample, after a two minute bleaching with a visible light source using the various borate salts.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein, the term "alkyl" refers to saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.). In certain embodiments, a straight chain or branched chain alkyl has 6 or fewer carbon atoms in its backbone (e.g., C1-C6 for straight chain, C3-C6 for branched chain) or 4 or fewer carbon atoms in its backbone (e.g., C1-C4 for straight chain, C3-C4 for branched chain). The term "C1-C6" alkyl refers to alkyl groups containing 1 to 6 carbon atoms. The term "C1-C4" alkyl refers to alkyl groups containing 1 to 4 carbon atoms. Moreover, the term alkyl includes both "unsubstituted alkyls" and "substituted alkyls," the latter of which refers to alkyl moieties having substituents replacing a hydrogen on one or more carbons of the hydrocarbon backbone. Such substituents can include, for example, (C1-C4)alkyl, (C1-C4)alkoxy, amino (including (C1-C4) alkylamino and (C1-C4)dialkylamino), aryls (including phenyl, naphthyl), cycloalkyls, hydroxyl, cyano, halogen, or nitro. Arylalkyls and cycloalkyls can be further substituted, e.g., with the substituents described above.

As used herein, the term "alkenyl" refers to unsaturated aliphatic groups analogous in length and possible substitution to the alkyls described above, but that contain at least one double bond. For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups. Moreover, the term "alkenyl" includes both "unsubstituted alkenyls" and "substituted alkenyls," the latter of which refers to alkenyl moieties having substituents replacing a hydrogen on one or more carbons of the hydrocarbon backbone. Such substituents can include, for example, (C1-C4)alkyl, (C1-C4)alkoxy, aryls, amino (including (C1-C4)alkylamino and (C1-C4)dialkylamino), hydroxyl, cyano, halogen, or nitro.

As used herein, the term "alkynyl" refers to unsaturated aliphatic groups analogous in length and possible substitution to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), or branched-chain alkynyl groups. Moreover, the term "alkynyl" includes both "unsubstituted alkynyls" and "substituted alkynyls," the latter of which refers to alkynyl moieties having substituents replacing a hydrogen on one or more carbons of the hydrocarbon backbone. Such substituents can include, for example, (C1-C4)alkyl, (C1-C4) alkoxy, aryls, amino (including (C1-C4)alkylamino and (C1-C4)dialkylamino), hydroxyl, cyano, halogen, or nitro.

As used herein, the term "alkoxy" refers to substituted and unsubstituted alkyl, alkenyl, and alkynyl groups covalently linked to an oxygen atom. Examples of alkoxy groups include, but are not limited to, methoxy, ethoxy, isopropyloxy, propoxy, butoxy, and pentoxy groups. In certain embodiments, a straight chain or branched chain alkoxy has 4 or fewer carbon atoms in its backbone (e.g., C1-C4 for straight chain, C3-C4 for branched chain). The term "C1-C4" alkyl refers to alkyl groups containing 1 to 4 carbon atoms.

As used herein, the term "amine" or "amino" refers to compounds or substituents where a nitrogen atom is covalently bonded to at least one carbon or heteroatom. The term includes "alkyl amino" which comprises groups and compounds wherein: the nitrogen is bound to at least one additional alkyl group. The term "dialkyl amino" includes groups wherein: the nitrogen atom is bound to at least two additional alkyl groups. In certain embodiments, these alkyl groups have 4 or fewer carbon atoms in their backbone (e.g., C1-C4 for straight chain, C3-C4 for branched chain). The term (C1-C4)alkylamino refers to groups and compounds, wherein the nitrogen is bound to at least one additional C1-C4 alkyl group. The term "(C1-C4)dialkylamino refers to groups and compounds, wherein the nitrogen is bound to at least two additional C1-C4 alkyl groups.

As used herein, the term "aryl" refers to groups, e.g., 5- and 6-membered single-ring aromatic groups, that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles," "heteroaryls" or "heteroaromatics." The aromatic ring can be substituted at one or more ring positions with such substituents as described above, as for example, (C1-C4) alkyl, (C1-C4) alkoxy, amino (including (C1-C4)alkylamino and (C1-C4)dialkylamino), hydroxyl, cyano, halogen, or nitro. Aryl groups can also be fused or bridged with alicyclic or heterocyclic rings which are not aromatic so as to form a polycycle (e.g., tetralin). The term heteroaryl includes unsaturated cyclic compounds such as azirine, oxirene, dithiete, pyrroline, pyrrole, furan, dihydrofuran, dihydrothiophene, thiophene, pyrazole, imidazole, oxazole, thiazole, isothiazole, 12,2,3-triazole, 1,2,4, triazole, dithiazole, tetrazole, pyridine, pyran, pyrimidine, pyran, thiapyrane, diazine, thiazine, dioxine, triazine and tetrazene.

As used herein, the term "antibody" refers to an immunoglobulin that specifically binds to and is thereby defined as complementary with a particular spatial and polar organization of another molecule. The antibody may be monoclonal or polyclonal and may be prepared by techniques that are well known in the art such as immunization of a host and collection of sera (polyclonal), or by preparing continuous hybrid cell lines and collecting the secreted protein (monoclonal), or by cloning and expressing nucleotide sequences or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM. Functional antibody fragments may include portions of an antibody capable of retaining binding at similar affinity to full-length antibody (for example, Fab, Fv and F(ab').sub.2, or Fab'). In addition, aggregates, polymers, and conjugates of immunoglobulins or their fragments may be used where appropriate so long as binding affinity for a particular molecule is substantially maintained.

As used herein, the term "binder" refers to a molecule that may bind to one or more targets in the biological sample. A binder may specifically bind to a target. Suitable binders may include one or more of natural or modified peptides, proteins (e.g., antibodies, affibodies, or aptamers), nucleic acids (e.g., polynucleotides, DNA, RNA, or aptamers); polysaccharides (e.g., lectins, sugars), lipids, enzymes, enzyme substrates or inhibitors, ligands, receptors, antigens, or haptens. A suitable binder may be selected depending on the sample to be analyzed and the targets available for detection. For example, a target in the sample may include a ligand and the binder may include a receptor or a target may include a receptor and the binder may include a ligand. Similarly, a target may include an antigen and the binder may include an antibody or antibody fragment or vice versa. In some embodiments, a target may include a nucleic acid and the binder may include a complementary nucleic acid. In some embodiments, both the target and the binder may include proteins capable of binding to each other.

As used herein, the term "biological sample" refers to a sample obtained from a biological subject, including sample of biological tissue or fluid origin obtained in vivo or in vitro. Such samples can be, but are not limited to, body fluid (e.g., blood, blood plasma, serum, or urine), organs, tissues, fractions, cells isolated from mammals including, humans and cell organelles. Biological samples also may include sections of the biological sample including tissues (e.g., sectional portions of an organ or tissue). Biological samples may also include extracts from a biological sample. Biological samples may comprise proteins, carbohydrates or nucleic acids.

A biological sample may be of prokaryotic origin, archaeal origin, or eukaryotic origin (e.g., insects, protozoa, birds, fish, and reptiles). In some embodiments, the biological sample is mammalian (e.g., rat, mouse, cow, dog, donkey, guinea pig, or rabbit). In certain embodiments, the biological sample is of primate origin (e.g., example, chimpanzee, or human).

As used herein, the term "control probe" refers to an agent having a binder coupled to a signal generator or a signal generator capable of staining directly, such that the signal generator retains at least 80 percent signal after contact with an electron transfer reagent and subsequent irradiation. A suitable signal generator in a control probe is not substantially inactivated, e.g., substantially bleached by photoactivated chemical bleaching, when contacted with the electron transfer reagent and irradiated. Suitable examples of signal generators may include a fluorophore that does not undergo bleaching under the conditions employed (e.g., DAPI).

As used herein, the term "enzyme" refers to a protein molecule that can catalyze a chemical reaction of a substrate. In some embodiments, a suitable enzyme catalyzes a chemical reaction of the substrate to form a reaction product that can bind to a receptor (e.g., phenolic groups) present in the sample. A receptor may be exogeneous (that is, a receptor extrinsically adhered to the sample or the solid-support) or endogeneous (receptors present intrinsically in the sample or the solid-support). Examples of suitable enzymes include peroxidases, oxidases, phosphatases, esterases, and glycosidases. Specific examples of suitable enzymes include horseradish peroxidase, alkaline phosphatase, β-D-galactosidase, lipase, and glucose oxidase.

As used herein, the term "enzyme substrate" refers to a chemical compound that is chemically catalyzed by an enzyme to form a reaction product. In some embodiments, the reaction product is capable of binding to a receptor present in the sample. In some embodiments, enzyme substrates employed in the methods herein may include non-chromogenic or non-chemiluminescent substrates. A signal generator may be attached to the enzyme substrate as a label.

As used herein, the term "electron transfer reagent" refers to a reagent that can engage in a photoreaction with a molecule capable of undergoing photoexcitation. This term also refers to a composition comprising a reagent that can engage in a photoreaction with a molecule capable of undergoing photoexcitation. In some embodiments, the molecule capable of undergoing photoexcitation may be a signal generator. In some embodiment, the electron transfer reagent may donate an electron to the signal generator in the course of a photoreaction. In alternative embodiments, the electron transfer reagent may accept an electron from the signal generator in the course of a photoreaction.

In some embodiments, the electron transfer reagent donating an electron to the signal generator in the course of a photoreaction may be a borate salt including the photo-induced chemical bleaching agent used in the invention for quenching eosin fluorescence. In alternative embodiments, the electron transfer reagent accepting an electron from the photoexcited molecule may be an onium salt [e.g., diphenyliodonium hexafluorophosphate (DPI) or dimethylphenacylsulfonium tetrafluoroborate (DMPS)], or tetrabutylammonium butyltriphenylborate (TBAB). An electron transfer reagent may include one or more chemicals that can engage in a photoreaction with a molecule capable of undergoing photoexcitation. The molecule capable of undergoing photoexcitation may be a signal generator. An electron transfer reagent may be contacted with the sample in the form of a solid, a solution, a gel, or a suspension. Other suitable electron transfer reagents may include sulfinates, enolates, carboxylates (e.g., ascorbic acid), organometallics and amines (e.g., triethanolamine, and N-phenylglycine). These and other electron transfer reagents have been previously described (see, e.g., Macromolecules 1974, 7, 179-187; Photogr. Sci. Eng. 1979, 23, 150-154; Topics in Current Chemistry, Mattay, J., Ed.; Springer-Verlag: Berlin, 1990, Vol. 156, pp 199-225; and Pure Appl. Chem. 1984, 56, 1191-1202.).

As used herein, the term "fluorophore" or "fluorescent signal generator" refers to a chemical compound, which when excited by exposure to a particular wavelength of light, emits light at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methylcoumarin (AMC, Coumarin 120), 7-amino-trifluoromethylcouluarin (Coumaran 151), cyanosine; 4',6-diaminidino-2-phenylindole (DAPI), 5',5''-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, cyanines, pyrelium dyes, squaraines, 1,3-dichloro-7-hydroxy-9,9-dimethyl-2(9H)-Acridinone (DDAO), and dimethylacridinone (DAO). In some embodiments, the fluorophore can be cyanine, rhodamine, BODIPY or 1,3-dichloro-7-hydroxy-9,9-dimethyl-2 (9H)-Acridinone (DDAO) dyes. In a preferred embodiment, the fluorophore is a cyanine dye. In a further embodiment, the cyanine dye is Cy3 or Cy5.

As used herein the term "H&E stain" generally refers to hematoxylin and eosin Y stain (H&E stain or HE stain). A histological section stained with H&E is often termed "H&E section", "H+E section", or "HE section". The staining method involves application of hemalum, which is a complex formed from aluminum ions and oxidized haematoxylin. These colors nuclei of cells (and a few other objects, such as keratohyalin granules) blue. The nuclear staining is followed by counterstaining with an aqueous or alcoholic solution of eosin Y, which colors other, eosinophilic structures in various shades of red, pink and orange.

The staining of nuclei by hemalum does not require the presence of DNA and is probably due to binding of the dye-metal complex to arginine-rich basic nucleoproteins such as histones. The eosinophilic structures are generally composed of intracellular or extracellular protein. The Lewy bodies and Mallory bodies are examples of eosinophilic structures. Most of the cytoplasm is eosinophilic. Red blood cells are stained intensely red.

As demonstrated in the Examples, eosin Y analogues such as eosin-B, phloxin B or erythrosine may be used in the place of eosin Y to obtain comparable H&E stains. As used herein in the term eosin analog refers to a chromogenic acidophilic dye that can be used in place of eosin Y to substantially stain the same morphological features as eosin Y and provides similar color images as those obtained with eosin Y under optimized conditions.

Thus, the term "H&E stain" also encompasses the use of these eosin Y analogues in obtaining a histological stain. These alternatives to eosin Y have lower intrinsic fluorescence and may be preferred for certain staining procedures.

As used herein the term charge transfer reagent refers to a chemical reagent that can form a charge transfer complex with eosin and in the process quenches eosin fluorescence. Examples of charge transfer reagents include but are not limited to p-quat, di-quat, phenylene diamine dihydrochloride.

As used herein, the term "in situ" generally refers to an event occurring in the original location, for example, in intact organ or tissue or in a representative segment of an organ or tissue. In some embodiments, in situ analysis of targets may be performed on cells derived from a variety of sources, including an organism, an organ, tissue sample, or a cell culture. In situ analysis provides contextual information that may be lost when the target is removed from its site of origin. Accordingly, in situ analysis of targets describes analysis of target-bound probe located within a whole cell or a tissue sample, whether the cell membrane is fully intact or partially intact where target-bound probe remains within the cell. Furthermore, the methods disclosed herein may be employed to analyze targets in situ in cell or tissue samples that are fixed or unfixed.

As used herein, the terms "irradiation" or "irradiate" refer to act or process of exposing a sample or a solution to non-ionizing radiation. In some embodiments, the non-ionizing irradiation has wavelengths between 350 nm and 1.3 μm. In preferred embodiments, the non-ionizing radiation is visible light of 400-700 nm in wavelength. Irradiation may be accomplished by exposing a sample or a solution to a radiation source, e.g., a lamp, capable of emitting radiation of a certain wavelength or a range of wavelengths. In some embodiments, a molecule capable of undergoing photoexcitation is photoexcited as a result of irradiation. In some embodiments, the molecule capable of undergoing photoexcitation is a signal generator, e.g., a fluorescent signal generator. In some embodiments, irradiation of a fluorescent signal generator initiates a photoreaction between the fluorescent signal generator and the electron transfer reagent. In some embodiments, irradiation initiates a photoreaction substantially inactivates the signal generator by photoactivated chemical bleaching.

Optical filters may be used to restrict irradiation of a sample or a solution to a particular wavelength or a range of wavelengths. In some embodiments, the optical filters may be used to restrict irradiation to a narrow range of wavelengths for selective photoexcitation of one or more molecules capable of undergoing photoexcitation. The term "selective photoexcitation" refers to an act or a process, whereby one or more molecules capable of undergoing photoexcitation are photoexcited in the presence of one or more other molecules capable of undergoing photoexcitation that remain in the ground electronic state after irradiation.

In some embodiments, the molecule capable of undergoing photoexcitation is a fluorescent dye, e.g., a cyanine dye. In one further embodiment, irradiation limited to a range of wavelengths between 520-580 nm is used for selective photoexcitation of a Cy3 dye. In another further embodiment, irradiation limited to a range of wavelengths between 620-680 nm is used for selective photoexcitation of a Cy5 dye. In alternative embodiments, irradiation of a sample at a specific wavelength may also be accomplished by using a laser.

As used herein, the term "peroxidase" refers to an enzyme class that catalyzes an oxidation reaction of an enzyme substrate along with an electron donor. Examples of peroxidase enzymes include horseradish peroxidase, cytochrome C peroxidase, glutathione peroxidase, microperoxidase, myeloperoxidase, lactoperoxidase, or soybean peroxidase.

As used herein, the term "peroxidase substrate" refers to a chemical compound that is chemically catalyzed by peroxidase to form a reaction product. In some embodiments, peroxidase substrates employed in the methods herein may include non-chromogenic or non-chemiluminescent substrates. A fluorescent signal generator may be attached to the peroxidase substrate as a label.

As used herein, the term "bleaching", "photoactivated chemical bleaching" or "photoinduced chemical bleaching" refers to an act or a process whereby a signal generated by a signal generator is modified in the course of a photoreaction. In certain embodiments, the signal generator is irreversibly modified.

In some embodiments, the signal is diminished or eliminated as a result of photoactivated chemical bleaching. In some embodiments, the signal generator is completely bleached, i.e., the signal intensity decreases by about 100%. In some embodiments, the signal is an optical signal, and the signal generator is an optical signal generator. The term "photoactivated chemical bleaching" is meant to exclude photobleaching, or loss of signal (e.g., fluorescent signal) that may occur in the absence of electron transfer reagent, e.g., after continued irradiation of a signal generator, such as a fluorophore, or after its continued exposure to light.

As used herein, the term "photoexcitation" refers to an act or a process whereby a molecule transitions from a ground electronic state to an excited electronic state upon absorption of radiation energy, e.g. upon irradiation. Photoexcited molecules can participate in chemical reactions, e.g., in electron transfer reactions. In some embodiments, a molecule capable of undergoing photoexcitation is a signal generator, e.g., a fluorescent signal generator.

As used herein, the term "photoreaction" or a "photoinduced reaction" refers to a chemical reaction that is initiated and/or proceeds as a result of photoexcitation of at least one reactant. The reactants in a photoreaction may be an electron transfer reagent and a molecule capable of undergoing photoexcitation. In some embodiments, a photoreaction may involve an electron transfer from the electron transfer reagent to the molecule that has undergone photoexcitation, i.e., the photoexcited molecule. In alternative embodiments, a photoreaction may also involve an electron transfer from the molecule that has undergone photoexcitation to the electron transfer reagent. In some embodiments, the molecule capable of undergoing photoexcitation is a fluorescent signal generator, e.g., a fluorophore. In some embodiments, photoreaction results in irreversible modification of one or more components of the photoreaction. In some embodiments, photoreaction substantially inactivates the signal generator by photoactivated chemical bleaching.

In some embodiments, the photoreaction may involve intermolecular electron transfer between the electron transfer reagent and the photoexcited molecule, e.g., the electron transfer occurs when the linkage between the electron transfer reagent and the photoexcited molecule is transitory, forming just prior to the electron transfer and disconnecting after electron transfer.

In some embodiments, the photoreaction may involve intramolecular electron transfer between the electron transfer reagent and the photoexcited molecule, e.g. the electron transfer occurs when the electron transfer reagent and the photoexcited molecule have been linked together, e.g., by covalent or electrostatic interactions, prior to initiation of the electron transfer process. The photoreaction involving the intramolecular electron transfer can occur, e.g., when the molecule capable of undergoing photoexcitation and the electron transfer reagent carry opposite charges and form a complex held by electrostatic interactions. For example, a cationic dye, e.g., a cationic cyanine dye and triphenylbutyl borate anion may form a complex, wherein intramolecular electron transfer may occur between the cyanine and borate moieties upon irradiation.

As used herein, the term "probe" refers to an agent having a binder and a label, such as a signal generator or an enzyme. In some embodiments, the binder and the label (signal generator or the enzyme) are embodied in a single entity. The binder and the label may be attached directly (e.g., via a fluorescent molecule incorporated into the binder) or indirectly (e.g., through a linker) and applied to the biological sample in a single step. In alternative embodiments, the binder and the label are embodied in discrete entities (e.g., a primary antibody capable of binding a target and an enzyme or a signal generator-labeled secondary antibody capable of binding the primary antibody). When the binder and the label (signal generator or the enzyme) are separate entities they may be applied to a biological sample in a single step or multiple steps. As used herein, the term "fluorescent probe" refers to an agent having a binder coupled to a fluorescent signal generator. In some embodiments, the probe may comprise an optical signal generator, such that the signal observed/detected is an optical signal. In some embodiments, the probe may comprise a fluorescent signal generator, such that the signal observed/detected is a fluorescent signal.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal. Examples of signal generators include one or more of a chromophore, a fluorophore, or a Raman-active tag. As stated above, with regard to the probe, the signal generator and the binder may be present in a single entity (e.g., a target binding protein with a fluorescent label) in some embodiments. Alternatively, the binder and the signal generator may be discrete entities (e.g., a receptor protein and a labeled-antibody against that particular receptor protein) that associate with each other before or upon introduction to the sample.

In some embodiments, the signal generator may be an optical signal generator. In some embodiments, the optical signal generator may be a fluorescent signal generator, e.g., a fluorophore. In preferred embodiments, the fluorescent signal generator may be a cyanine dye, e.g., Cy3, Cy5 or Cy7. In some embodiments, the signal generator, e.g., a fluorophore, may be charged. In one embodiment, the signal generator is a cationic fluorescent dye.

As used herein, the term "solid support" refers to an article on which targets present in the biological sample may be immobilized and subsequently detected by the methods disclosed herein. Targets may be immobilized on the solid support by physical adsorption, by covalent bond formation, or by combinations thereof. A solid support may include a polymeric, a glass, or a metallic material. Examples of solid supports include a membrane, a microtiter plate, a bead, a filter, a test strip, a slide, a cover slip, and a test tube.

As used herein, the term "specific binding" refers to the specific recognition of one of two different molecules for the other compared to substantially less recognition of other molecules. The molecules may have areas on their surfaces or in cavities giving rise to specific recognition between the two molecules arising from one or more of electrostatic interactions, hydrogen bonding, or hydrophobic interactions. Specific binding examples include, but are not limited to, antibody-antigen interactions, enzyme-substrate interactions, polynucleotide interactions, and the like. In some embodiments, a binder molecule may have an intrinsic equilibrium association constant (KA) for the target no lower than about 105 M-1 under ambient conditions such as a pH of about 6 to about 8 and temperature ranging from about 0° C. to about 37° C.

As used herein, the term "target" refers to the component of a biological sample that may be detected when present in the biological sample. The target may be any substance for which there exists a naturally occurring specific binder (e.g., an antibody), or for which a specific binder may be prepared (e.g., a small molecule binder or an aptamer). In general, a binder may bind to a target through one or more discrete chemical moieties of the target or a three-dimensional structural component of the target (e.g., 3D structures resulting from peptide folding). The target may include one or more of natural or modified peptides, proteins (e.g., antibodies, affibodies, or aptamers), nucleic acids (e.g., polynucleotides, DNA, RNA, or aptamers); polysaccharides (e.g., lectins or sugars), lipids, enzymes, enzyme substrates, ligands, receptors, antigens, or haptens. In some embodiments, targets may include proteins or nucleic acids.

The disclosed methods relate generally to detection of multiple targets in a single biological sample which is subjected to Hematoxylin and eosin stain (H&E) at some time during its analysis and allows for removal of the H&E signals from the tissue. The same tissue may then be subjected to immunofluorescence and FISH staining. In some embodiments, methods of detecting multiple targets in a single H&E stained biological sample using the same detection channel are disclosed. The invention includes embodiments that relate to methods applicable in analytical, diagnostic, or prognostic applications such as analyte detection, fluorescence-activated cell sorting (FACS), histochemistry, immunohistochemistry, or immunofluorescence. In some embodiments, the methods disclosed herein may be particularly applicable in histochemistry, immunostaining, immunohistochemistry, immunoassays, immunofluorescence or fluorescence in situ hybridization.

The method disclosed comprises optionally detecting the hematoxylin and eosin staining of the biological sample containing multiple targets; removing fluorescent H&E signal from the hematoxylin and eosin stained biological sample; and detecting additional features or targets in the biological sample. The biological sample is thus available, after an H&E stain, for further molecular analysis either by IHC, IF or FISH, and the same detection channel for eosin is available for detection of such molecular interactions.

In some embodiments, the method disclosed comprises using a low fluorescent eosin analogue for the H&E stain. Therefore the removing step includes a wash using a buffered aqueous solution. Exemplary low fluorescence eosin includes eosin-B, phloxin B and erythrosin. In some embodiments, the buffered aqueous solution is the solution buffered in phosphate buffered saline (PBS). In some embodiments, the solution is buffered at pH of 5-9. In a preferred embodiment, the pH of the solution is 6-8.

In some embodiments, the method disclosed comprises a protocol wherein in the first step hematoxylin and a majority of the eosin is removed from the H&E stained sample by different washing protocols. In following steps, the sample is contacted with a charge transfer reagent to quench the residual fluorescence; and optionally washed using a buffered aqueous solution to remove excess reagent and charge transfer complex. Exemplary charge transfer reagents are selected from Methyl Viologen (p-Quat), diquat and phenylene diamine dihydrochloride salts.

Contacting of the sample with the charge transfer reagent may be carried out for a predetermined amount of time. In some embodiments, the contacting step may be performed for about 20 seconds to about 100 minutes, preferably for about 1 minute to about 60 minutes, and even more preferably, for about 5 minutes to about 20 minutes. In some embodiments, the contacting step may be performed until no residual signal is detected from the eosin stain.

In some embodiments, the contacting step may be carried out at a temperature of 4-50° C., more preferably, at a temperature of 20-30° C.

In some embodiments, the contacting step may be carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

In some embodiments, the method disclosed comprises a protocol wherein in the first step hematoxylin and a majority of the eosin is removed from the H&E stained sample by different washing protocols. In following steps, the sample is contacted with hydroxyl radicals generated in situ; and in some embodiments hydroxyl radical generation is enhanced by irradiation with light.

Irradiation of the sample contacted with the reagents for generating hydroxyl radicals (peroxide and a metal salt, e.g. a ferrous salt) may be carried out for a predetermined amount of time. The duration of irradiation may depend on the desired duration of the photoreaction between the hydroxyl radicals and the eosin stain. In some embodiments, the irradiation step may be performed for about 20 seconds to about 60 minutes, preferably for about 20 seconds to about 15 minutes, and even more preferably, for about 20 seconds to about 5 minutes. In some embodiments, the irradiation step may be performed until no residual signal is detected from the eosin stain.

In some embodiments, the irradiation step may be carried out at a temperature of 4-50° C., more preferably, at a temperature of 20-30° C.

In some embodiments, the irradiation step may be carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is acidic.

In some embodiments, the method disclosed comprises a two-step protocol wherein in the first step hematoxylin and a majority of the eosin is removed from the H&E stained sample by different washing protocols. In a second step, irreversible quenching of residual eosin fluorescence by photo-induced electron transfer based chemistry, herein referred to as Photoinduced Chemical Bleaching (PICB), is then applied to remove the residual eosin signal. This PICB process involves excitation of eosin in the presence of an electron donor or acceptor. Following excitation an electron is transferred between the dye and either the donor or the acceptor and the resultant reactive dye undergoes further reaction or rearrangements with an accompanied change in optical properties. For example, a biological sample is stained with eosin. After imaging and removal of hematoxylin and partial removal of eosin, the slide is flooded with a borate salt buffer and light from mercury, halogen or xenon lamp, an LED or another light source is shined on the tissue to bleach the eosin signal.

While not definitive, the mechanism of eosin bleaching may be based on electron transfer from borate to the eosin molecule after the photoexcitation of the eosin followed by generation of an alkyl radical from borate radical degradation. Subsequent reaction of the dye with the alkyl radical or other species in the buffer may then destroy the dye signal. In some embodiments, the photoreaction comprises intermolecular electron transfer. In other embodiments, the photoreaction comprises intramolecular electron transfer.

In some embodiments, the eosin signal is irreversibly modified. In some embodiments, the eosin signal is irreversibly modified by a photoreaction that inactivates the signal generator, e.g. eosin, by photoactivated chemical bleaching.

In some embodiments, the electron transfer agent which undergoes photo induced chemical bleaching (PICB) is a borate salt. In some embodiments, the borate salt is represented by the following structural formula:

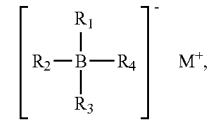

wherein:

each R1, R2, and R3 is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro;

R4 is an alkyl, an alkenyl, or an akynyl, wherein said alkyl, alkenyl, or alkynyl is optionally substituted with one or more substituents selected from the group consisting of (C1-C4)alkyl, (C1-C4)alkoxy, aryl, (C1-C4) alkylamino, amino, hydroxyl, cyano, halogen, or nitro; and M+ is selected from the group consisting of organic and inorganic cations.

In some embodiments, each R1, R2, and R3 is an optionally substituted aryl. In some embodiments, said aryl is phenyl. In some embodiments, said phenyl is an unsubstituted phenyl.

In some embodiments, R4 is an optionally substituted alkyl. In some embodiments, R4 is butyl or benzyl.

In some embodiments, each R1, R2, and R3 is an optionally substituted aryl and R4 is an optionally substituted alkyl. In a further embodiment, each R1, R2, and R3 is phenyl and R4 is butyl or benzyl, and the borate salt is triphenylbutyl borate salt or triphenylbenzyl borate salt.

In some embodiments, M+ is an inorganic cation. In some embodiments, the inorganic cation is Li+, Na+ or K+.

The following structures are non-limiting examples of borate salts useful as PICB agents:

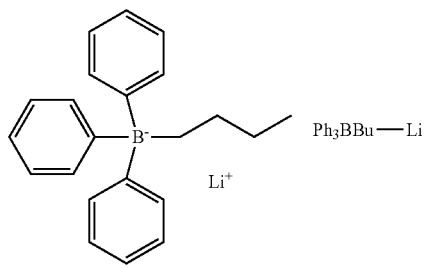

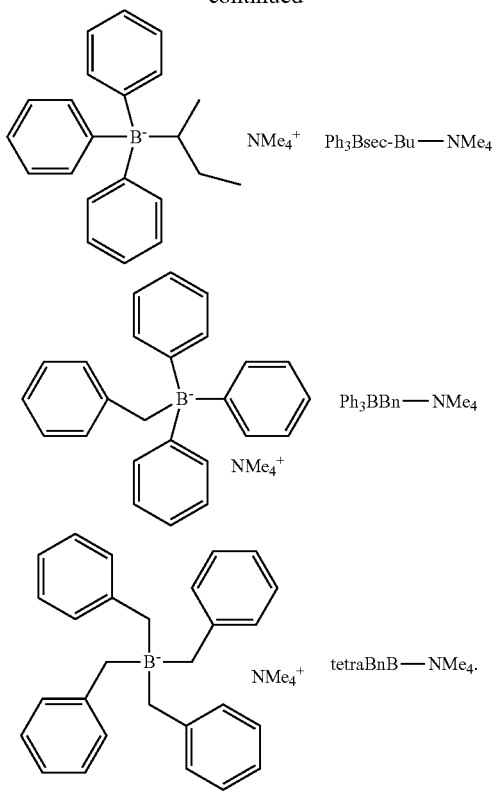

In some embodiments, the PICB agent may be in the form of a solution. In one embodiment, the PICB agent is present in the form of a buffered aqueous solution. In some embodiments, the electron transfer reagent may be a borate salt. In further embodiments, the PICB agent may be a triphenyl butyl borate salt present at a concentration of 0.001 mM to 1000 mM. In a preferred embodiment, the concentration of triphenyl butyl borate is from 20 mM to 100 mM. In certain embodiments, the PICB agent may be a triphenyl benzyl borate present at a concentration of 0.001 mM to 10 mM and more preferably at a concentration of 200 uM to 10 mM.

Irradiation of the sample contacted with the PICB agent may be carried out for a predetermined amount of time. The duration of irradiation may depend on the desired duration of the photoreaction between the PICB agent and the eosin stain. In some embodiments, the irradiation step may be performed for about 20 seconds to about 60 minutes, preferably for about 20 seconds to about 15 minutes, and even more preferably, for about 20 seconds to about 5 minutes. In some embodiments, the irradiation step may be performed until no residual signal is observed/detected from the eosin stain. In some embodiments, the irradiation step may be performed at room temperature.

In some embodiments, the photoreaction is carried out at a temperature of 4-50° C., more preferably, at a temperature of 20-30° C.

In some embodiments, the photoreaction is carried out in a solution. In some embodiments, the solution is a buffered solution. In a further embodiment, the buffered solution is the solution buffered in phosphate buffered saline (PBS). In some embodiments, the solution is buffered at pH of 5-9. In a preferred embodiment, the pH of the solution is 6-8.

Figure 2:
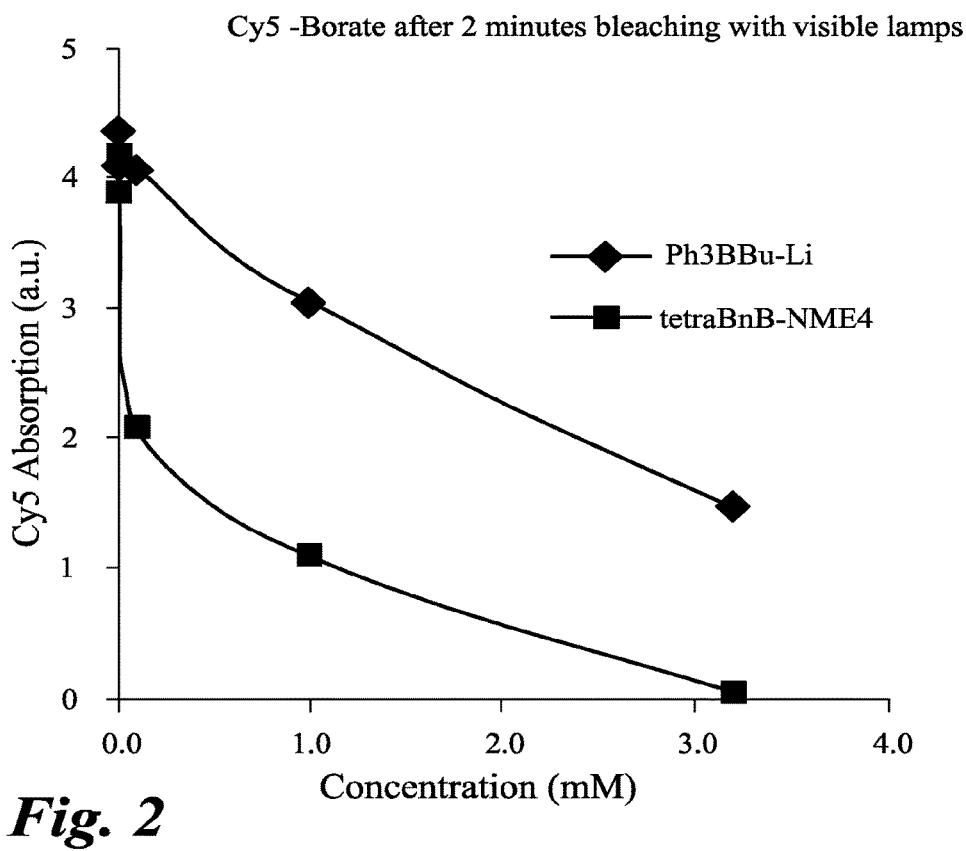
FIG. 2 is a graphical representation of the effect of borate concentration after two minutes of bleaching with a visible light source.

Results of photobleaching of representative borate salts are shown graphically in FIG. 1 and FIG. 2. FIG. 1 is a standardized graph showing the percentage of signal intensity, compared to a control sample, after a two minute bleaching with a visible light source using the various borate salts. FIG. 2 is a graphical representation of the effect of borate concentration after two minutes of bleaching with visible light sources. As shown concentration of the two borate salts were varied (0 to 3.25 mM). The decay in Cy5 intensity is shown as concentration increases.

In some embodiments, a characteristic of the eosin signal may be detected after the fluorescent signal removal to determine the effectiveness of the bleaching. For example, a color may be detected before the fluorescent signal removal step and the color may be absent after the fluorescent signal removal step. Alternatively, fluorescence may be measured before and after signal removal as colorimetric detection is not as sensitive as fluorescent detection and even in the absence of color, substantial fluorescence may remain. In some embodiments, a decrease in signal intensity by a predetermined amount may be referred to as signal modification, or bleaching. In some embodiments, modification of the signal may refer to a decrease in the signal intensity by an amount in a range of greater than about 50 percent. In some embodiments, modification of the signal may refer to a decrease in the signal intensity by an amount in a range of greater than about 60 percent. In some embodiments, modification of the signal may refer to a decrease in the signal intensity by an amount in a range of greater than about 80 percent. In some embodiments, modification of the signal may refer to a decrease in the signal intensity by an amount in a range of greater than about 90 percent. In some embodiments, modification of the signal may refer to a decrease in the signal intensity by an amount in a range of greater than about 95 percent. In some embodiments, modification of the signal may refer to a decrease in the signal intensity by an amount in a range of about 100 percent, or to complete bleaching.

As such, in some embodiments, the methods disclosed herein may be employed in a process where the H&E stained sample, when fluorescent signals are removed, may be subjected to additional immunostaining procedures. For instance, the additional immunostainng procedures available when the fluorescent signals of the H&E stained sample has been removed may allow detection of a plurality of targets in the same biological sample with little or no effect on the integrity of the biological sample. Detecting the targets in the same biological sample may further provide spatial information about the targets in the biological sample. Methods disclosed herein may also be applicable in analytical applications where a limited amount of biological sample may be available for analysis and the same sample may have to be processed for multiple analyses. Methods disclosed herein may also facilitate multiple analyses of solid-state samples (e.g., tissue sections) or samples adhered to a solid support. Furthermore, the same detection channel may be employed for detection of different targets in the sample, enabling fewer chemistry requirements for analyses of multiple targets. The methods may further facilitate analyses based on detection methods that may be limited in the number of simultaneously detectable targets because of limitations of resolvable signals. For example, using fluorescent-based detection, the number of targets that may be simultaneously detected may be limited to about four as only about four fluorescent signals may be resolvable based on their excitation and emission wavelength properties. In some embodiments, the methods disclosed herein may allow detection of greater than four targets using fluorescent-based detection system.

Methods of iteratively analyzing an individual sample have been described in U.S. Pat. No. 7,629,125 and U.S. Pat. No. 7,741,046. In particular, U.S. Pat. No. 7,741,046 provides methods of detecting multiple targets in a biological sample that involve the use of oxidation for inactivating signal generators (e.g., for bleaching fluorescent dyes.) The oxidation reaction is accomplished by using oxidizing reagents, such as hydrogen peroxide as well as photoxidation and which are herein incorporated by reference. Additional methods of iterative analyses are described in the literature, e.g. Borduchi A. et. al., Genetics and Molecular Biology 1999, 22, 173-175, Toth Z E and Mezey E., J Histochem Cytochem 2007, 55, 545-554, & Zrazhevskiy P and Gao X, Nature Communications 2013, 4, 1619, and are included herein by reference.

In still other methods, the methods employ, e.g., a signal cycling process wherein in each cycle, a photoreaction step allows the same signal generators, e.g., fluorophores, to be reused in the subsequent cycle to detect additional markers, e.g., proteins. These methods can be employed, e.g., for sequentially analyzing a biological sample to discern, among other things, the presence, absence, concentration, and/or spatial distribution of multiple biological targets in a biological sample. The photoreaction step can include applying an electron transfer agent, e.g., a borate salt, and initiating a photoreaction, e.g., by irradiating the sample with visible light, to inactivate the signal generator, e.g., fluorescent dye.

Figure 3A:
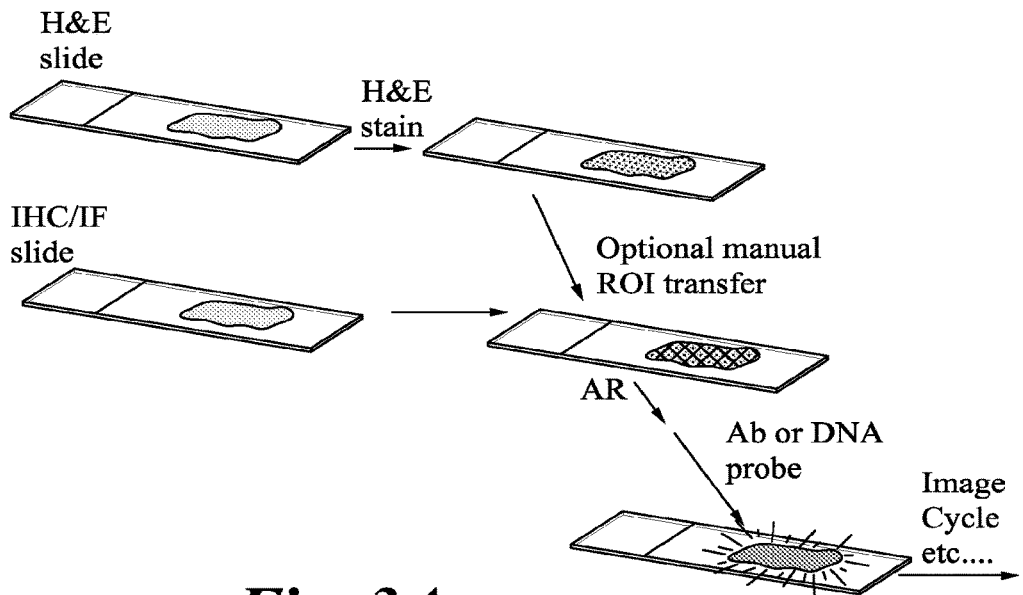
FIG. 3 is an illustrated example of a current approach to H&E and IHC or IF imaging using two slides (FIG. 3A) compared to single slide approach using PICB to remove eosin staining (FIG. 3B).

Certain process improvement afforded by the invention is illustrated in FIG. 3. FIG. 3A is a representation of a current approach wherein two separate slides are processed for H&E and IHC, IF or FISH. In some instances, an H&E slide is initially processed and stained to identify a region of interest (ROI). A second slide, which may be part of a serial tissue section is then processed, for example using IHC or FISH, using the information obtained from the H&E staining of the first slide.

Figure 3B:
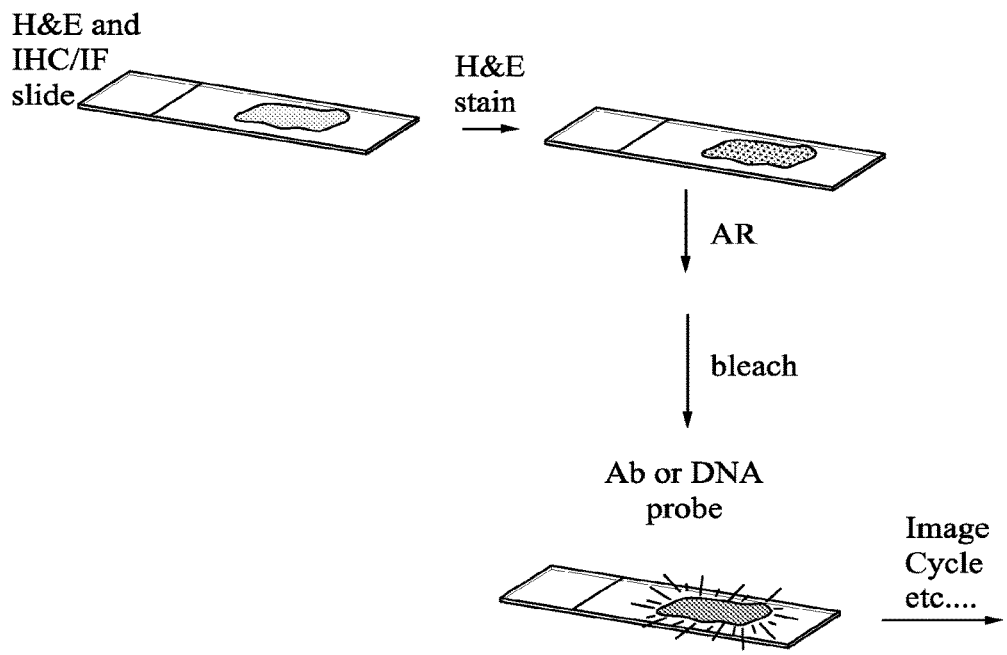

An improvement to the method is shown in one embodiment as illustrated in FIG. 3B. As shown, a single slide is capable of combining both H&E and IHC, IF or FISH staining. The slide is subjected to the H&E staining and undergoes PICB. The same slide is then subjected to IHC, IF or FISH protocol. The process allows information to be obtained on single slide and replaces the need for ROI transfer time, which may be in the range of 2 or more hours, to be processed with less than 0.5 hours of H&E removal. In addition to the time savings, the process also saves tissue and reduces error in that morphological and molecular information is now obtainable from the same section.

In addition to improvements in process time and tissue retention, in some embodiments the method also allows for the removal of eosin fluorescence by PICB such that the residual eosin fluorescence does not interfere with subsequent imaging.

Figure 4:
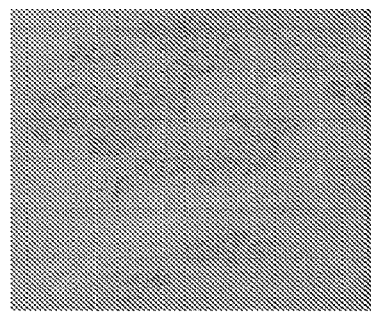
FIG. 4 shows residual eosin fluorescence (bottom image) after H&E removal by conventional methods while brightfield image in the middle appears to show complete removal of hematoxylin and eosin.
Figure 4:
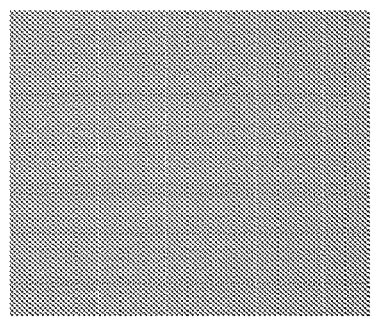
Figure 4:
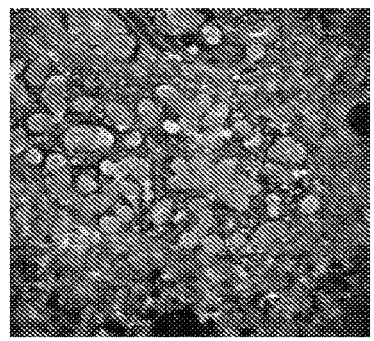

As shown in FIG. 4 removal of H&E by conventional methods while appears to remove both hemotoxylin and eosin Y as shown in brightfield image (middle image), fluorescence imaging show significant residual eosin Y fluorescence (bottom image) that can interfere with subsequent fluorescence based detection.

Figure 5:
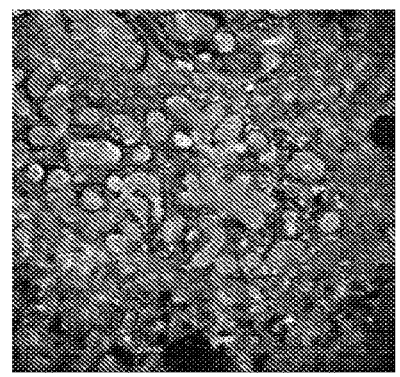
FIG. 5 shows almost complete removal of residual eosin fluorescence by photo-induced chemical bleaching.
Figure 5:
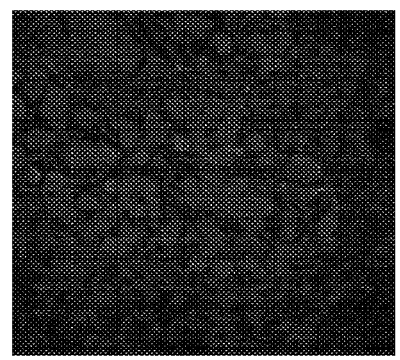
Figure 5:
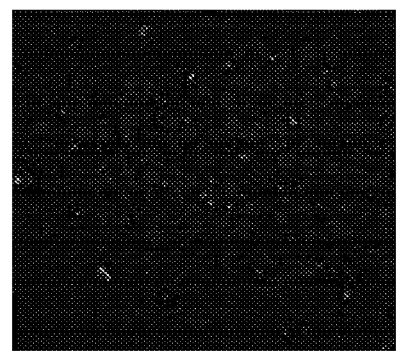

FIG. 5 shows the same region of interest (ROI) whereby the residual eosinfluorescence is removed by PICB treatment. The eosin fluorescence is significantly reduced (middle image) and is comparable to the autofluorescence in the control slide which was not subjected to H&E staining (bottom image).

Figure 6:
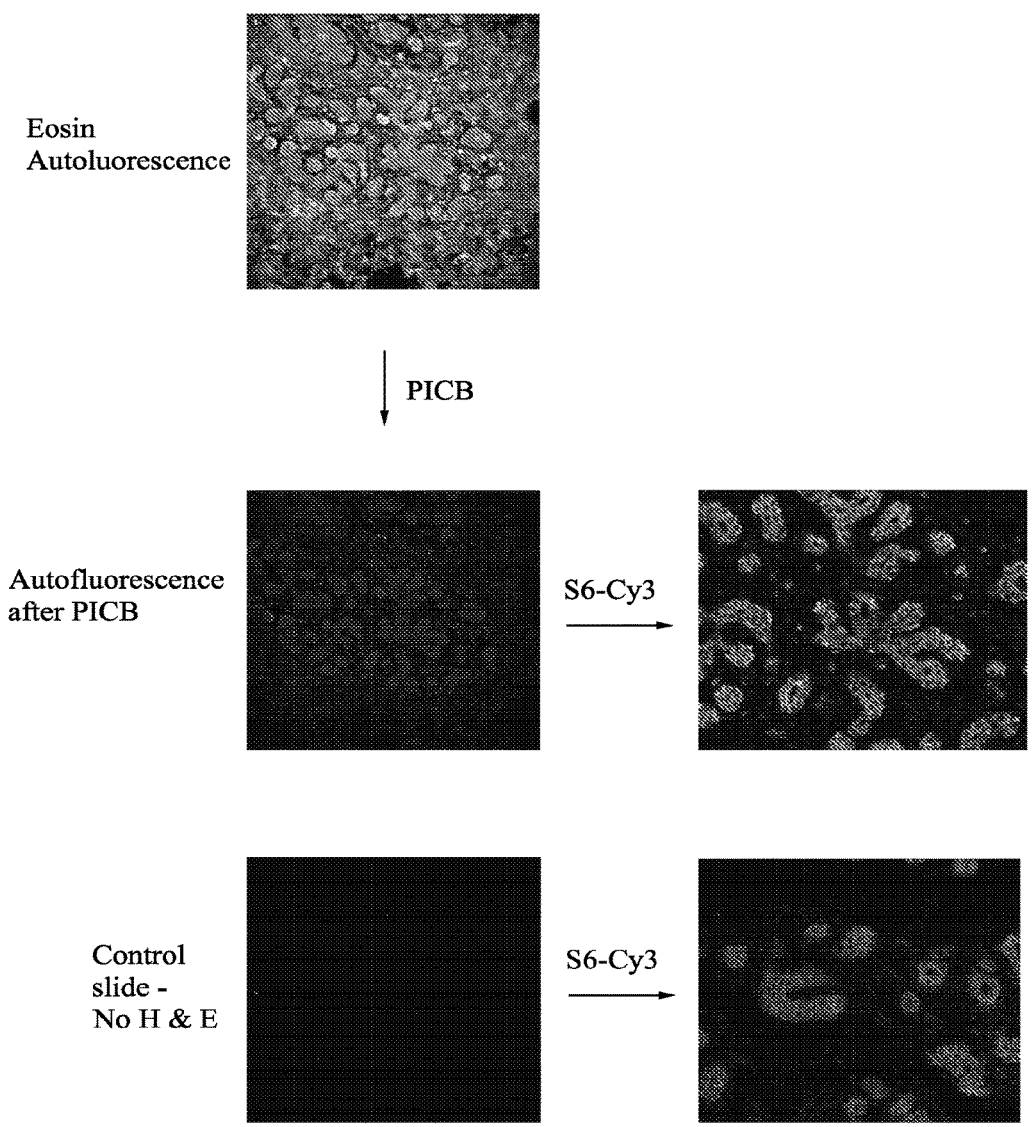
FIG. 6 shows immunofluorescence staining of a PICB bleached H&E slide is comparable to immunostaining on a control slide that was not subjected to H&E staining.

Subsequent staining of the slide with Cy3-labeled antibody targeting S6 protein (FIG. 6) shows specific staining of protein (middle panel, left image—after eosin fluorescence removal by PICB, right S6 stained image after PICB) that is easily discernible and is comparable to signal detected on the controlled slide (bottom panel, left image—tissue autofluorescence of a slide that was not subjected to H&E, right image, S6 stained image).

Figure 12:
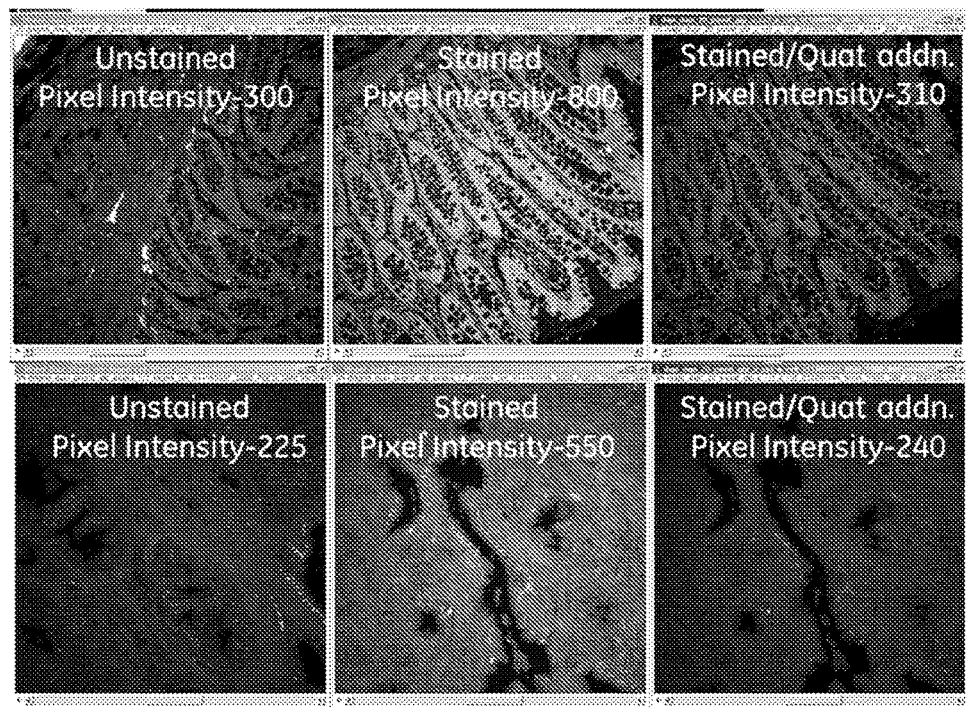
FIG. 12 showing human Colon (top) and Prostate (bottom) tissue sections—Comparison of unstained (left), Eosin stained and subjected to rehydration and antigen retrieval (middle, showing residual eosin fluorescence) and after physical quenching of Eosin fluorescence by a charge transfer reagent (right, incubated in 500 µL of 20 mg/mL p-Quat in water for 20 minutes, washed with 1×PBS, 3×, coverslipped and imaged).
Figure 13:
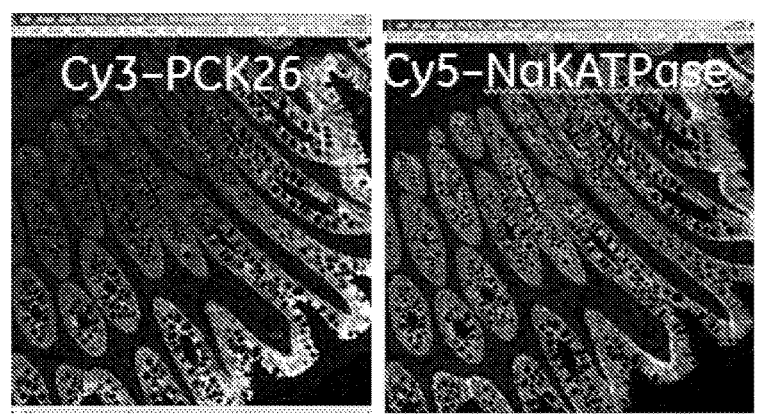
FIG. 13 showing staining of colon with PCK26-Cy3 and NaKATpase-Cy5 after p-Quat treatment/washing.
Figure 14:
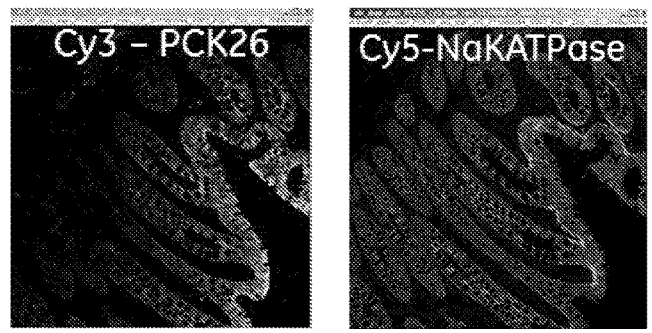
FIG. 14 showing staining of Prostate with PCK26-Cy3 and NaKATpase-Cy5 in the presence of p-Quat in mounting media.

Similar results are obtained when an H&E slide is contacted by charge transfer reagents, with a subsequent wash to remove excess salt. FIG. 12. The slide may be stained with molecular probes, with no detectable difference in signal detection. FIG. 13. Alternatively, charge transfer reagent may be added just prior to detection of molecular signals, to suppress fluorescent signals from H&E staining. FIG. 14.

Figure 15:
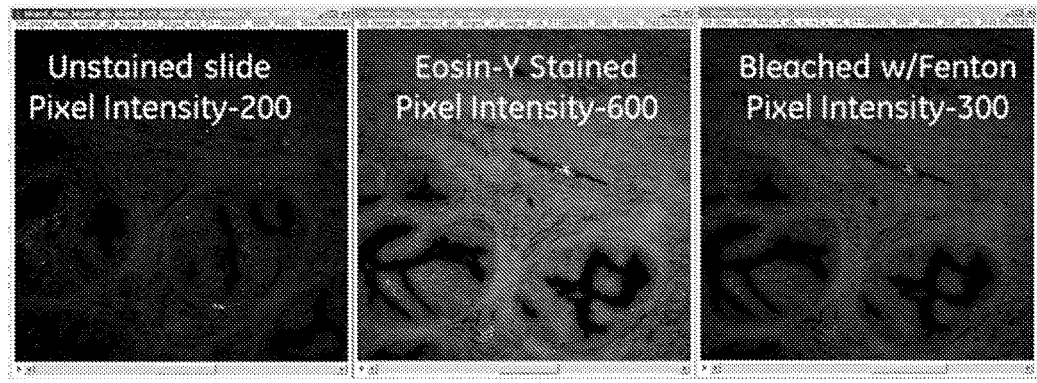
FIG. 15 showing human Prostate tissue sections—Comparison of unstained (left), Eosin stained and subjected to rehydration and antigen retrieval (middle, showing residual eosin fluorescence) and after bleaching of Eosin fluorescence by light catalyzed generation of hydroxyl radicals in situ.

Hydroxy radicals may be used to remove residual eosin fluorescence as well, which may be generated in situ using hydrogen peroxide and a metal salt and may be further catalyzed by light irradiation. After signal removal excess reagents and byproducts are washed off prior to subsequent analysis. FIG. 15.

Figure 16:
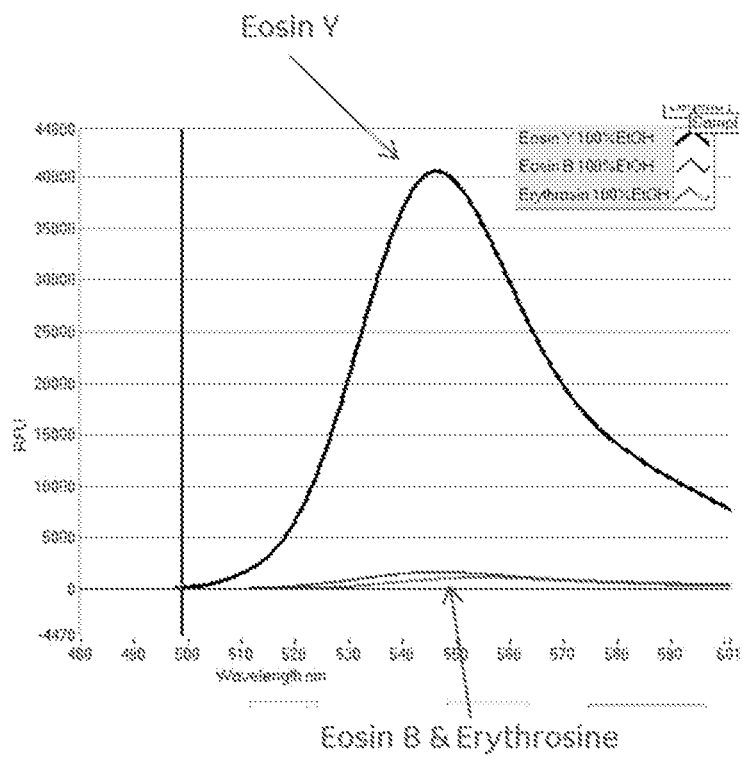
FIG. 16 shows relative fluorescence emission spectra of various Eosin Derivatives in ethanol solvent.
Figure 17:
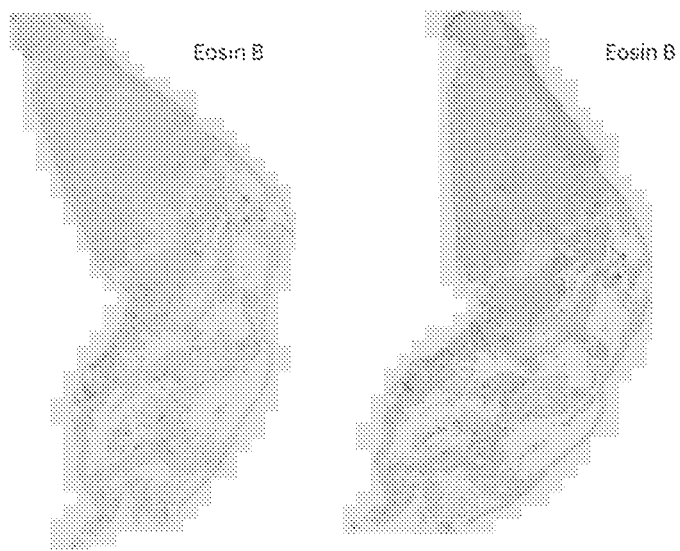
FIG. 17: Example results from evaluation of different protocols for staining with eosin B. Eosin B staining is dramatically affected by the protocol used.
Figure 18:
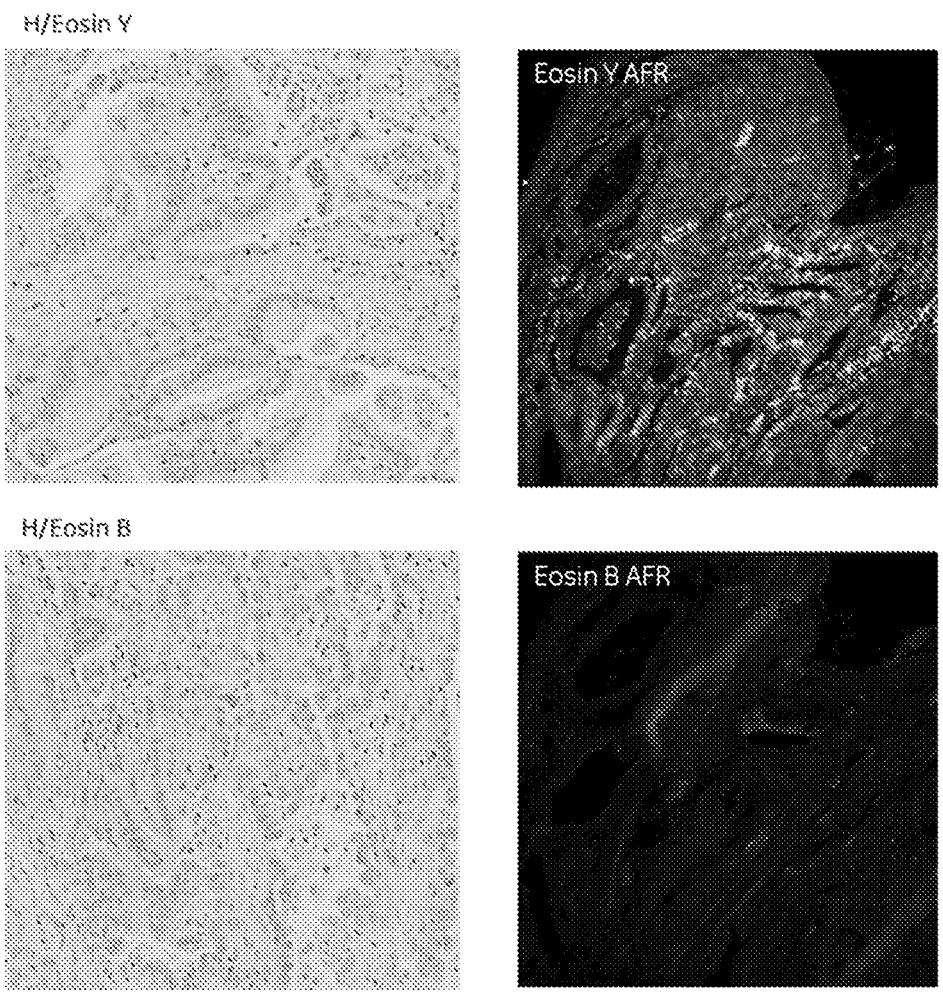
FIG. 18: Staining with Eosin Y and Eosin B shows no change in H&E stain but a large difference in residual fluorescence. AFR: autofluorescence.
Figure 19:
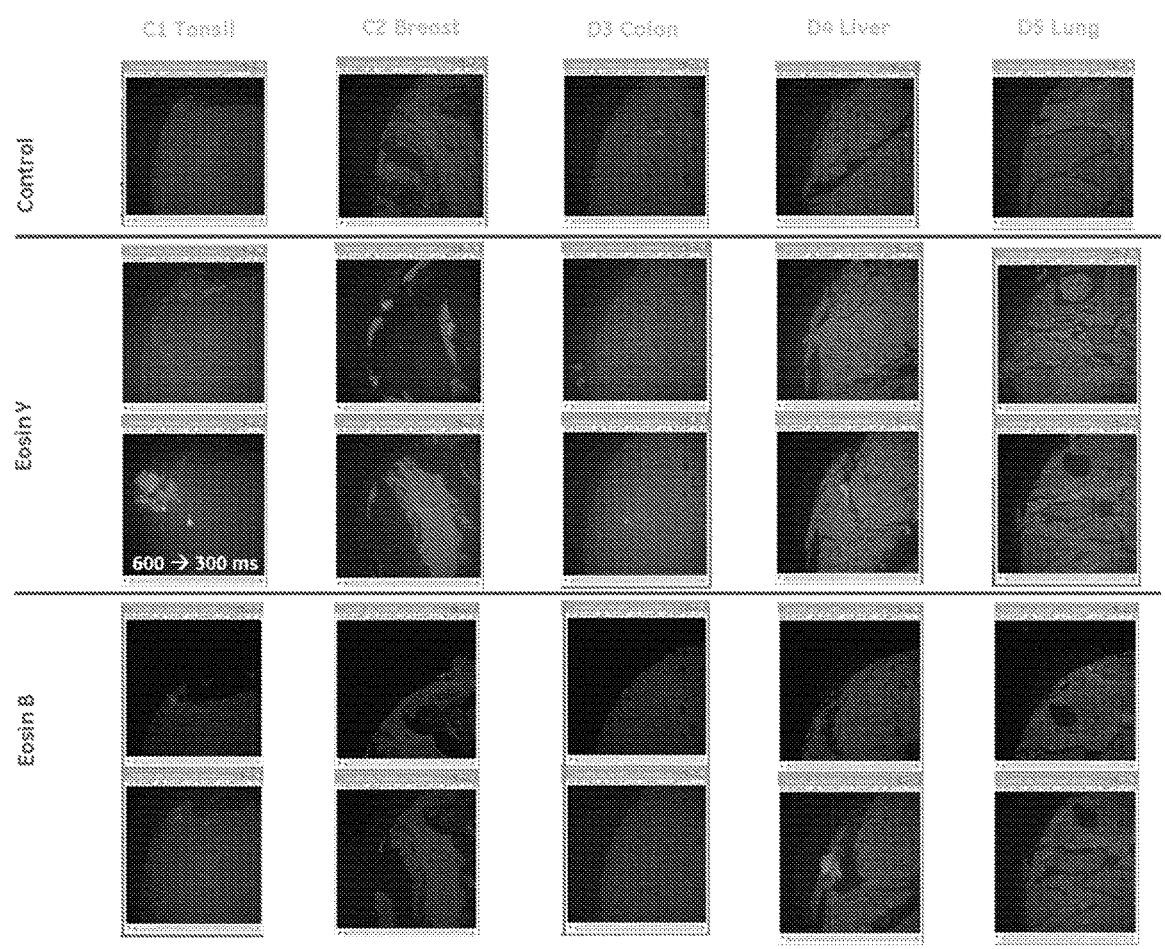
FIG. 19: Images of residual autofluorescence in different tissue types after H&E staining using different eosin analogs and after antigen retrieval to remove H&E signal: Top: control unstained slides subjected to standard clearing, hydration and antigen retrieval showing intrinsic tissue autofluorescence, middle: tissue samples stained with eosin Y showing higher background than control indicating not all the eosin Y could be removed, and bottom: tissue samples stained with eosin B showing comparable autofluorescence to control unstained slide indicating practically complete removal of eosin B signal.

Alternative, low fluorescence eosin analogues may be used to replace Eosin Y in the H&E staining process. FIGS. 16, 17 and 18. A simple wash step effectively removes the fluorescence signal from these alternative eosin analogues. FIG. 19.

In some embodiments, the method allows for H&E staining, the removal of the fluorescent signal of the H&E staining, and subsequent high throughput multiplexing biological sample analysis that includes a signal cycling process, wherein in each cycle, staining and imaging is followed by a signal inactivation step such as by applying an electron transfer reagent and irradiation of the biological sample or stripping the probes. The method allows rapid signal cycling without significantly modifying the components of the biological sample that are different from the probe.

Figure 7:
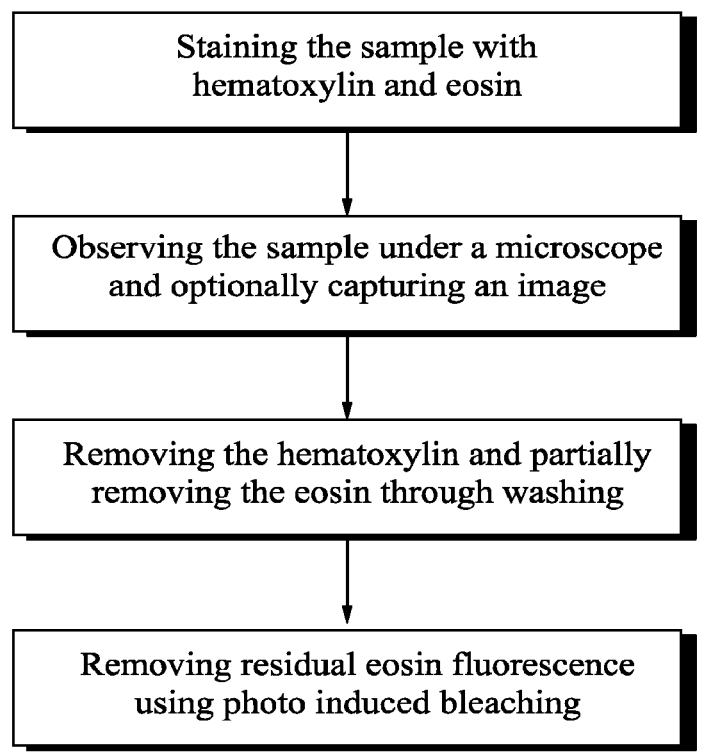
FIG. 7 is a flow chart of steps involved in the process of using a slide for H&E and removing the H&E signal so the slide can be subsequently used for other analysis.

FIG. 7 is a flow chart representing one embodiment of the invention. As shown, the method comprises providing a biological sample and:
 (a) staining the biological sample with hematoxylin and eosin;
 (b) detecting the sample using a microscope and optionally capturing an image;
 (c) optionally removing the hematoxylin and partially removing the eosin through washing; and
 (d) removing residual eosin fluorescence using, e.g., photo induced chemical bleaching.

In still other embodiments, the methods may further comprise the step of antigen retrieval (AR) after the H&E staining protocol. The antigens, thus exposed may then be subjected to further H&E signal removal and immunohistochemical staining, such as IF. This is further illustrated in FIG. 8-10.

Generally an antigen target may be present on the surface of a biological sample (for example, an antigen on a surface of a tissue section). In some embodiments, an antigen target may not be inherently present on the surface of a biological sample and the biological sample may have to be processed to make the target available on the surface (e.g., antigen recovery, enzymatic digestion or epitope retrieval). An antigen retrieval step may be performed as such involving high temperature heating in acid and or base. Such procedures are further described in U.S. patent application Ser. No. 13/551,190 filed Jul. 17, 2012 herein incorporated by reference.

Figure 8:
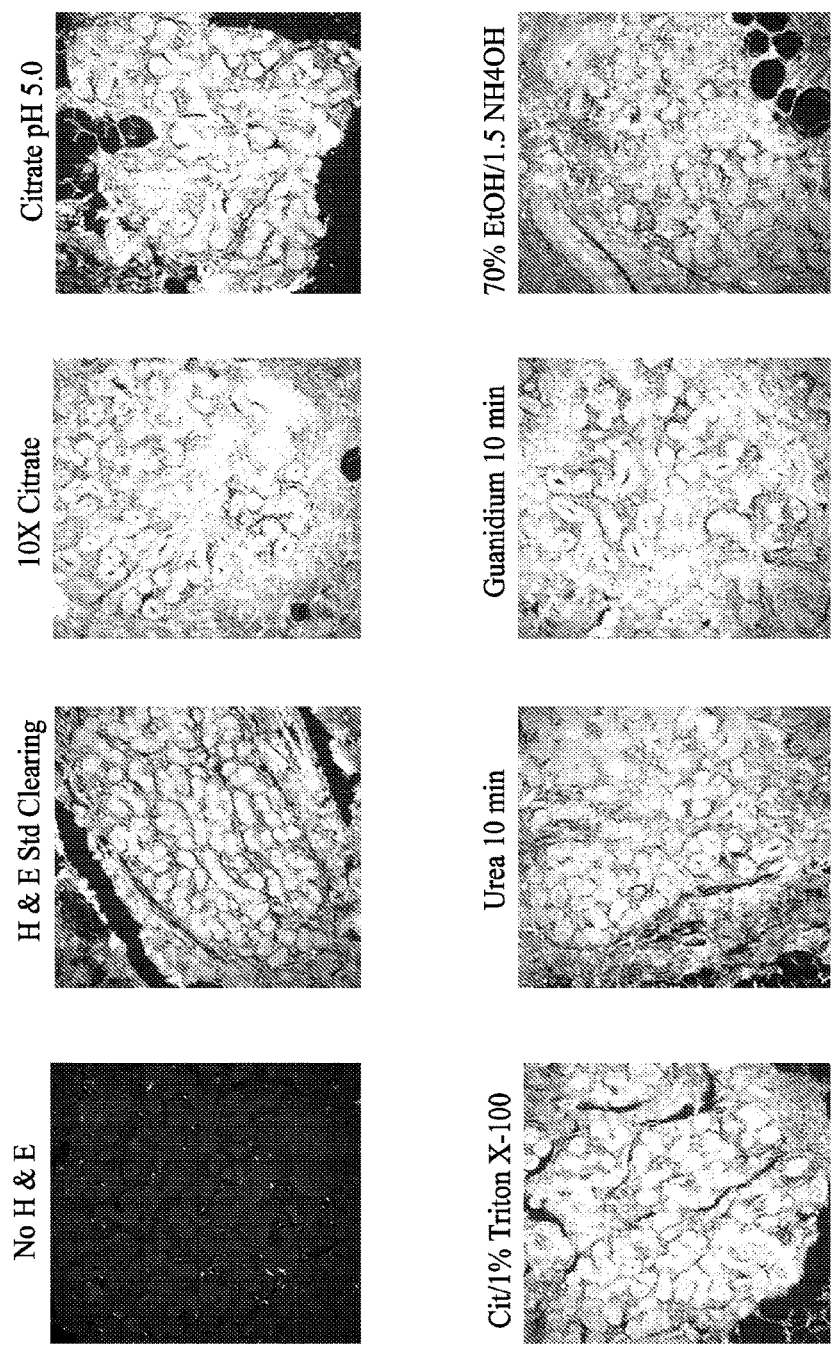
FIG. 8 shows various failed attempts to remove eosin fluorescence using buffers/salts, detergents, denaturants and solvents.
Figure 9:
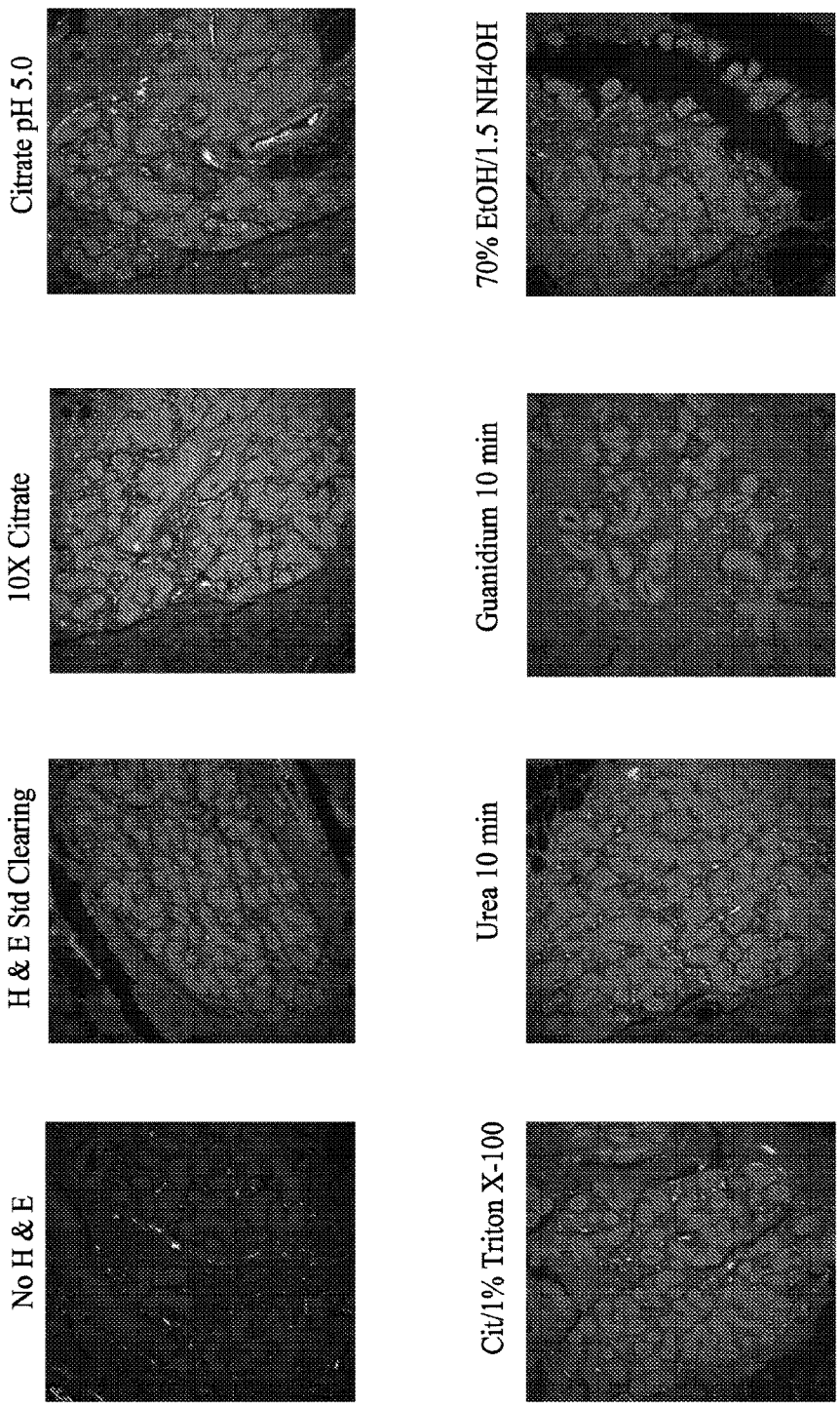
FIG. 9 shows almost complete removal of eosin fluorescence with PICB of slides subjected to various treatments shown in FIG. 8.
Figure 10:
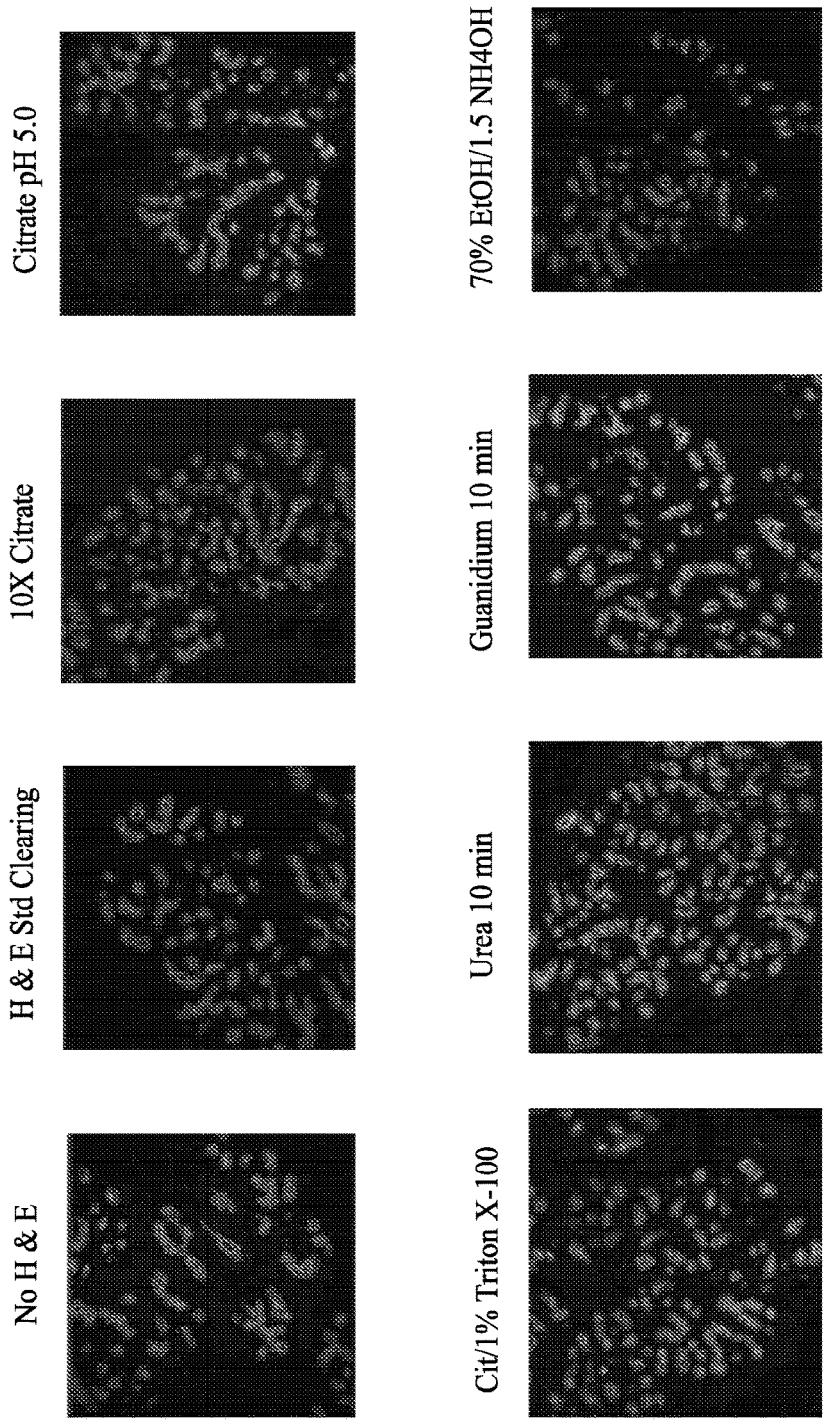
FIG. 10 shows grayscale images of pan-cytokeratin staining with Cy3-labeled AE1 antibody on the slides bleached by PICB (shown in FIG. 9)

In some embodiments, eosin signal may be partially removed during the antigen retrieval process before removal of the residual signal. The antigen retrieval process itself or other washings steps using a variety of additives are unable to remove all fluorescent signal from eosin Y. FIG. 8. shows various unsuccessful attempts at removing the residual eosin Y fluorescence by making changes to the slide processing process (slide clearing and antigen retrieval) for immunohistochemistry by changing salt concentration, pH, addition of other salts or protein denaturants. Processes such as PICB is necessary to remove the signal as shown in FIG. 9 while maintaining tissue antigenicity as shown by staining the same slides with a Cy3-labeled panCK (Cy3-AE1) antibody (FIG. 10).

In some embodiments, aside from the sample preparation procedures discussed above, the biological sample may be subjected to further treatment. For example, in some embodiments, the tissue section may be subjected to a blocking step to minimize any non-specific binding. Following the preparation of the sample, the sample may be contacted with a binder solution (e.g., labeled-antibody solution in an immunofluorescence procedure) for a sufficient period of time and under conditions suitable for binding of binder to the target protein (e.g., antigen in an immunofluroescence procedure).

In some embodiments, the biological sample may be contacted with more than one binder in the contacting step. The plurality of binders may be capable of binding different target proteins in the biological sample. For example, a biological sample may include two target proteins: target1 and target2 and two sets of binders may be used in this instance: binders1 (capable of binding to target1) and binders2 (capable of binding to target2). As such, plurality of binders may be contacted with the biological sample simultaneously. For example staining with different fluorescently-labeled antibodies such as AR, ER, p53, Her2, smooth muscle actin, keratin, and pan-cadherin biomarkers, as a single mixture). The method further includes detecting signals from the one or more binders generating an image of the sample. A photo-induced chemical bleaching agent may be applied thereby initiating a photoreaction that modifies the signal of one or more binders.

Figure 11:
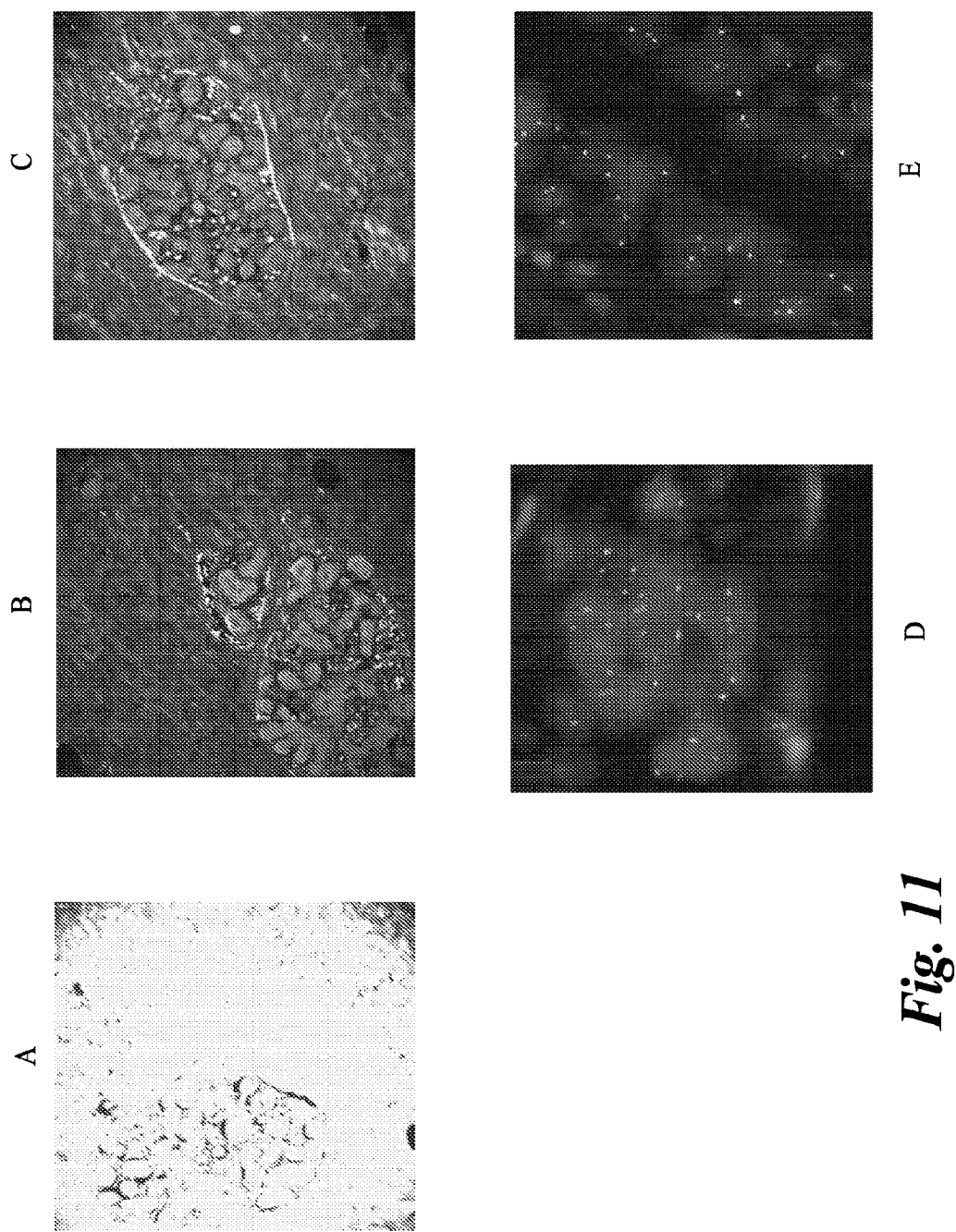
FIG. 11 shows FISH on PICB bleached H&E slide is comparable to FISH on a control slide that was not subjected to H&E staining.

In some embodiments, the sample may then undergo further sequential staining and detection of targets in multiple rounds of staining and signal removal. As such the method is applicable to using IHC, IF or FISH after a slide has been subjected to H&E staining. For example, FIG. 11 shows a fluorescence based image of an H&E stained slide (a) which after H&E removal using both washing and PICB steps was subjected to FISH with HER2 and CEP17 probes. A non-H&E stained slide was used as control. As the figure shows, after bleaching the residual fluorescence of the bleached slide which was treated with 40 mM dicyclopentyldiphenylborate lithium salt for 15 min 24 W lamp (b) is comparable to the tissue autofluorescence of the control slide (c) showing autofluorecence. Both slides (b and c) provide good staining with FISH probes (d and e respectively).

As such, the method includes but is not limited to methods that may also include detection and analysis of biological samples containing multiple targets and binding at least one probe having a binder coupled for example, to an enzyme to one or more target present in the sample. In yet other embodiments, the methods described above provide a series of at least two images depicting optically labeled biological targets which may be detected, in an detecting step using a variety of methods.

In some embodiments, a control probe may be employed in the methods disclosed herein to provide for co-registration of multiple molecular information (obtained through the iterative probing steps) and the morphological information (obtained, e.g., using DAPI). In some embodiments, methods disclosed herein may include co-registration of multiple fluorescent images with bright-field morphological images obtained using the aforementioned H&E protocol. In some embodiments, the probes employed in the iterative probing steps may not have any common compartmental information that may be used to register with the initial H&E images. A control probe like a DAPI nuclear stain may be employed to co-register the nucleus stained with hematoxylin in the bright-field images with the fluorescent images. The fluorescent images and the bright-field images may be co-registered using image registration algorithms that may be grouped in two categories: intensity-based and feature-based techniques.

In some embodiments, the imaging, which may also be referred to as detecting steps, include co-localizing at least two targets in the sample. Methods for co-localizing targets in a sample are described in U.S. patent application Ser. No. 11/686,649, entitled "System and Methods for Analyzing Images of Tissue Samples", filed on Mar. 15, 2007; U.S. Pat. No. 8,131,476, entitled "System and Method for Co-Registering Multi-Channel Images of a Tissue Micro Array"; U.S. Pat. No. 8,060,348, entitled "System and Methods for Scoring Images of a Tissue Micro Array"; and U.S. Pat. No. 8,036,462, entitled "Automated Segmentation of Image Structures"; each of which is herein incorporated by reference.

In the detecting steps, a signal from a signal generator may be detected using a detection system. The nature of the detection system used may depend upon the nature of the signal generators used. The detection system may include a charge coupled device (CCD) detection system, a fluorescent detection system, an electrical detection system, a photographic film detection system, a chemiluminescent detection system, an enzyme detection system, an optical detection system, a near field detection system, or a total internal reflection (TIR) detection system.

One or more of the aforementioned techniques may be used to detect one or more characteristics of a signal from a signal generator (coupled with a binder or coupled with an enzyme substrate). In some embodiments, signal intensity, signal wavelength, signal location, signal frequency, or signal shift may be determined using one or more of the aforementioned techniques. In some embodiments, one or more aforementioned characteristics of the signal may be detected, measured, and recorded.

In some embodiments, one or more of the aforementioned methods may be automated and may be performed using automated systems. In some embodiments, all the steps may be performed using automated systems.

The methods disclosed herein may find applications in analytic, diagnostic, and therapeutic applications in biology and in medicine. In some embodiments, the methods disclosed herein may find applications in histochemistry, particularly, immunohistochemistry. Analysis of cell or tissue samples from a patient, according to the methods described herein, may be employed diagnostically (e.g., to identify patients who have a particular disease, have been exposed to a particular toxin or are responding well to a particular therapeutic or organ transplant) and prognostically (e.g., to identify patients who are likely to develop a particular disease, respond well to a particular therapeutic or be accepting of a particular organ transplant). The methods disclosed herein, may facilitate accurate and reliable analysis of a plurality (e.g., potentially infinite number) of targets (e.g., disease markers) from the same biological sample.

EXAMPLES

The following examples are intended only to illustrate methods and embodiments in accordance with the invention, and as such should not be construed as imposing limitations upon the claims.

Example 1. Preparation of Tissue Samples

Human breast tissue array samples were obtained as tissue slides embedded in paraffin from Clarient, Huntsville, Ala. Slides were baked at 60° C. for 15 minutes and then H&E stained.

Example 2. H&E Staining

All the slides were stained with hematoxylin and eosin following the standard regressive protocol listed below. After staining, images were obtained as described below in Table 1. In the procedure the slide with tissue is baked at 60° C. for 15 minutes prior to the first XYLENE step. The Hematoxylin and Eosin were filtered before each use. Coverslip was applied directly out of xylene to prevent the slide from drying before coverslipping.

TABLE 1

Standard Regressive protocol H&E Staining

| Solution | Time | Vendor | Manufacture/Catalog # |
| --- | --- | --- | --- |
| Xylene | 5 minutes | Fisher Sci. | Fisher Chemical #C8H10 |
| Xylene | 3 minutes | Fisher Sci. | Fisher Chemical #C8H10 |
| 100% Alcohol | 1 minute | VWR | EMD-HARLECO, 100% Alcohol blend #34172-020 |
| 100% Alcohol | 1 minute | VWR | EMD-HARLECO, 100% Alcohol blend #34172-021 |
| 95% Alcohol | 1 minute | VWR | EMD-HARLECO, Dehydration Alcohol 95%, #65348 |
| 95% Alcohol | 1 minute | VWR | EMD-HARLECO, Dehydration Alcohol 95%, #65349 |
| 80% Alcohol | 1 minute | VWR | EMD-HARLECO, Dehydration Alcohol 95%, #65350 |
| DI Water | 20-30 seconds | | |
| HEMATOXYLIN | 5 minutes | VWR | EMD-HARLECO, Gill Modified, solution 2, #65066-85 |
| DI Water | 5 quick dips | | |
| DI Water | 5 quick dips | | |
| 1% Acid alcohol | 1 quick dip | VWR | 99% 70% alcohol, 1% Hydrochloric Acid -EMD CHEMICALS #HX0603P-5 |
| DI Water | 5 quick dips | | |
| DI Water | 5 quick dips | | |
| Blueing | 2 minutes | VWR | EMD-HARLECO Staining Blueing Reagent #65354-85 |
| Running Water | 2 minutes | | |
| DI Water | 5 quick dips | | |
| 95% Alcohol | 30 seconds | VWR | EMD-HARLECO, Dehydration Alcohol 95%, #65348 |
| Eosin Y | 1½ minutes | VWR | EMD-HARLECO, 1% alcoholic solution #588X-75 |
| 95% Alcohol | 10 dips | VWR | EMD-HARLECO, Dehydration Alcohol 95%, #65348 |
| 95% Alcohol | 10 dips | VWR | EMD-HARLECO, Dehydration Alcohol 95%, #65348 |
| 100% Alcohol | 30 seconds | VWR | EMD-HARLECO, 100% Alcohol blend #34172-020 |
| 100% Alcohol | 30 seconds | VWR | EMD-HARLECO, 100% Alcohol blend #34172-020 |
| Xylene | 3 minutes | Fisher Sci. | Fisher Chemical #C8H10 |

Example 3. Imaging

Brightfield and Fluorescence images were taken for all the slides using Leica brightfield microscope and Olympus microscope respectively. For fluorescence, eosin stained images were collected in Cy2 (Ex: 482/35, Em: 536/40), Cy3 (Ex: 531/40, Em: 593/40), and Cy5 (Ex: 628/40, Em: 692/40) channels.

Example 4. Tissue Rehydration and Permeabilization

After imaging, samples were hydrated by washing in four solutions of ethanol with concentrations decreasing in the order of 100%, 95%, 70%, and 50% followed by a wash with 1× phosphate buffer saline (PBS, pH 7.4). After rehydration, the slides were washed with 1×PBS. A ten minute wash in 0.3% Triton X-100 in PBS was performed for membrane permeabilization of the tissue, followed by a wash with 1×PBS. The slides were then subjected to different buffers to attempt H&E removal.

Example 5. Antigen Retrieval

Hydrated slides were treated with dual-buffer heat-induced epitope retrieval. Slides were immersed in a preheated 70° C. Citrate Buffer pH 6.0 (Vector Unmasking Solution), further heated in a pressure cooker to a temperature of 110° C., held at this temperature for 4 minutes, and then gradually cooled (final temperature of 96° C.). Slides were in Citrate Buffer for a total of twenty minutes and then transferred to hot (96° C.) Tris-EDTA Buffer pH 9.0 and allowed to stand in the cooker at atmospheric pressure with gradual cooling for twenty minutes. This was followed by cooling down at room temperature for ten minutes and a series of washes in 1×PBS. Slides were imaged by brightfield and fluorescence microscopy. While bright-field images showed practically complete removal of hematoxylin and eosin colors, bright fluorescence was observed/detected from residual eosin.

Example 6. Attempted Removal of H&E without PICB

Slides were additionally subjected to following conditions in an attempt to remove H&E. 10× citrate (instead of standard 1× citrate during antigen retrieval for standard time of 20 minutes), citrate pH 5.0 (instead of standard citrate pH 6.0 during antigen retrieval for standard time of 20 minutes), citrate made in 1% triton X-100 (instead of standard citrate made in PBS during antigen retrieval for standard time of 20 minutes), 100 mM urea pH 4.5 (10 minute wash followed by 3 brief water washes before proceeding to antigen retrieval), 100 mM guanidinium pH 5.0 (10 minute wash followed by 3 brief water washes before proceeding to antigen retrieval), 70% ethanol in 1.5M NH4OH (instead of 70% ethanol in water during rehydration for standard 2×5 minutes).

Example 7. Blocking

Following antigen retrieval the slides were blocked against nonspecific binding by incubating overnight in a 10% donkey serum, 3% bovine serum albumin (BSA) solution at 4° C.

Example 8. Residual Eosin Bleaching

All H & E slides after blocking were treated with 40 mM of Dicyclopentyl diphenylborate (500 ul) and irradiated with 500 nm light for 30 minutes. Washed with 3×PBS to remove the residual borate.

Example 9. Immuno Staining

Slides were stained with DAPI and cover slipped. Images were taken at 20× prior to protein staining to see the autofluorescence of eosin in Cy2, Cy3 and Cy5 channels. Slides were decoverslipped in 1×PBS and stained with cytokeratin AE1-Cy3 conjugate diluted in 3% BSA in 1λ PBS. Incubation was for one hour at room temperature. After incubation, a series of washes in 1×PBS removed excess antibodies and slides were cover slipped. The samples were imaged.

Example 10. H&E and Fluorescence In Situ Hybridization (FISH) on the Same Slide Steps 1-7 were performed as described above in the Examples 1-5, 7 & 8. FISH protocol was then applied. Slides were decoverslipped after imaging and immersed in a prewarmed 0.1% pepsin solution for 8 minutes then placed in room temperature PBS for 2 minutes. Samples were re-fixed in 4% formalin for 10 minutes then washed 2×5 minutes in PBS. Slides were dehydrated in ethanol series 50%, 70%, and 95%, 2 minutes each and allowed to dry on benchtop for 10 minutes. Pre-mixed dual Her2/CEP17 probe was vortexed, spun, and added to samples. Samples were coverslipped and sealed with a rubber cement per usual practice. After allowing rubber cement to cure for 10 minutes, probes were hybridized in Thermobrite cycler: 80° C. denaturation for 10 minutes followed by 37° C. incubation overnight. Rubber cement removed and slides decoverslipped in preheated 37° C. 2×SSC for 5 minutes then transferred into preheated 72° C. 2×SSC, 0.3% NP-40 for 2 minutes. Slides were washed 2×2 minutes with 2×SSC, removed from buffer to dry, coverslipped with 4% DABCO in 90% glycerol/2× SSC, and imaged on an Olympus IX81 fluorescence microscope using a 40× objective for DAPI (2 ms), spectrum green (CEP17-200 ms), and spectrum orange (Her2-400 ms). A z-stack value of 12, gain of 10, and step size of 0.75μ were used.

Example 11. Residual Eosin Bleaching Using Charge Transfer Reagents (Fluorescence Quenching by Physical Means)

Slides were treated through all the steps described in examples 1-5 and imaged to capture residual autofluorescence. After antigen retrieval slides were treated with 2.5-20 mg/mL of Methyl Viologen (p-Quat), diquat or phenylene diamine dihydrochloride salts (500 ul) and incubated in a dark humidified chamber for 20 minutes. Slides were washed 3× with 1×PBS to remove the excess salts and imaged again prior to blocking and staining with a Cy3-labeled pan-cytokeratin antibody PKC26 and Cy5-labeled anti-NaKATPase antibody as described in examples 7 & 9. Slides were coverslipped and reimaged to capture protein staining. As shown in FIG. 12, after antigen retrieval, significant residual eosin fluorescence (FIG. 12, center images) remains as compared to the residual autofluorescence of an unstained serial section (FIG. 12, left images). After incubation with the charge transfer reagents, this residual autofluorescence can be readily quenched (FIG. 12, right images) and slides can be stained for molecular targets of interest (FIG. 13).

Example 12. Residual Eosin Bleaching Using Charge Transfer Reagents (Alternative Method)

Alternatively, the charge transfer reagents (2.5-20 mg/mL) were dissolved into the mounting media [90% Glycerol/4% propyl gallate and 1% DABCO]. Slides were subjected to steps described in examples 1-5, 7 and 9 (stained with Cy3-PKC26 and Cy5-NaKATPase) and coverslipped using the charge transfer reagents containing mounting media prior to imaging. As shown in FIG. 14, charge transfer reagents can be applied to quench eosin autofluorescence after the slides have been stained with dye labeled antibodies. Signal intensity appears slightly diminished; however, both targets can be readily detected.

Example 13. Residual Eosin Y Fluorescence Removal Using Light Catalyzed Hydroxyl Radical Generation Slides were treated through all the steps described in examples 1-5 and imaged to capture residual autofluorescence. After antigen retrieval the slides were incubated with a fresh mixture of 300 μL of $FeSO_4.7H_2O$-2.7 mg/50 mL in water and 300 μL of $H_2O_2$: 1.2 mg/mL. The slides were subjected to white light irradiation (aquatic lamps) for 10 mins. After irradiation the slides were washed 3× with 1×PBS to remove the excess reagents and imaged. Residual eosin fluorescence from the H&E staining is effectively bleached by hydroxyl radicals (FIG. 15).

Example 14. Use of Alternate Stains (Eosin B and Erythrosin)

Analogs of eosin Y, such as Eosin-B, Phloxin B and Erythrosin are orders of magnitude lower in fluorescence compared to Eosin-Y (FIG. 16) and also have high solubility in polar protic solvents such as alcohols and water which may allow their easy removal. One key requirement, however, is that they provide comparable H&E image to the H&E images obtained with hematoxylin and eosin Y.

a. Modified H&E Staining Protocol:

H&E protocol described in example 2 was optimized for each eosin analog by evaluating various compositions of solutions of eosin analogs (FIG. 17) and the following conditions (see modified protocol below) were identified to provide H&E stained images indistinguishable from those obtained with eosin Y (FIG. 18), as determined by a trained pathologist.

TABLE

Modified H&E staining protocol for staining with eosin B: The main difference is the use of 50% aqueous ethanol for staining with eosin B.

| Solution | Time | Vendor | Manufacture/Catalog # |
|---|---|---|---|
| Xylene | 5 minutes | Fisher Sci. | Fisher Chemical #C8H10 |
| Xylene | 3 minutes | Fisher Sci. | Fisher Chemical #C8H10 |
| 100% Alcohol | 1 minute | VWR | EMD-HARLECO, 100% Alcohol blend #34172-020 |
| 100% Alcohol | 1 minute | VWR | EMD-HARLECO, 100% Alcohol blend #34172-021 |
| 95% Alcohol | 1 minute | VWR | EMD-HARLECO, Dehydration Alcohol 95%, #65348 |
| 95% Alcohol | 1 minute | VWR | EMD-HARLECO, Dehydration Alcohol 95%, #65349 |
| 80% Alcohol | 1 minute | VWR | EMD-HARLECO, Dehydration Alcohol 95%, #65350 |
| DI Water | 20-30 seconds | | |
| HEMATOXYLIN | 5 minutes | VWR | EMD-HARLECO, Gill Modified, solution 2, #65066-85 |
| DI Water | 5 quick dips | | |
| DI Water | 5 quick dips | | |
| 1% Acid alcohol | 1 quick dip | VWR | 99% 70% alcohol, 1% Hydrochloric Acid -EMD CHEMICALS #HX0603P-5 |
| DI Water | 5 quick dips | | |
| DI Water | 5 quick dips | | |
| Blueing | 2 minutes | VWR | EMD-HARLECO Staining Blueing Reagent #65354-85 |
| Running Water | 2 minutes | | |
| DI Water | 5 quick dips | | |
| 95% Alcohol | 30 seconds | VWR | EMD-HARLECO, Dehydration Alcohol 95%, #65348 |
| EosinB | 1½ minutes | | EMD-HARLECO, 1% solution prepared in 50% ethanol |
| 95% Alcohol | 10 dips | VWR | EMD-HARLECO, Dehydration Alcohol 95%, #65348 |
| 95% Alcohol | 10 dips | VWR | EMD-HARLECO, Dehydration Alcohol 95%, #65348 |
| 100% Alcohol | 30 seconds | VWR | EMD-HARLECO, 100% Alcohol blend #34172-020 |
| 100% Alcohol | 30 seconds | VWR | EMD-HARLECO, 100% Alcohol blend #34172-020 |
| Xylene | 3 minutes | Fisher Sci. | Fisher Chemical #C8H10 | b. Removal of H&E Signal from H&E Generated Using Eosin B:

H&E slides stained with eosin B using the modified protocol were subjected to steps described in examples 3-5 and slides were imaged to capture residual fluorescence. An eosin Y stained slide using the protocol described in example 2 was used as a control and was processed through the same steps as eosin B stained slide. As shown in FIG. 18, eosin Y stained control slide has considerable residual fluorescence as expected from observations made earlier, but the autofluorescence of eosin B stained slide is comparable to an unstained slide control. Similar results were observed on several different tissue types representing major cancer types (FIG. 19).

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A method of analyzing a hematoxylin and eosin stained biological sample, comprising:
    (a) optionally detecting hematoxylin and eosin staining of a biological sample containing multiple targets and stained with hematoxylin and eosin;
    (b) removing fluorescent hematoxylin and eosin signals from the biological sample; and
    (c) detecting additional features or targets in the biological sample;
    wherein removing the fluorescent hematoxylin and eosin signals from the biological sample comprises:
        (1) washing the biological sample using a buffered aqueous solution to remove the hematoxylin and partially remove the eosin; and contacting the biological sample with a charge transfer reagent to quench residual fluorescence;
        (2) washing the biological sample using a buffered aqueous solution to remove the hematoxylin and partially remove the eosin; contacting the biological sample with hydrogen peroxide and a metal salt to generate hydroxyl radicals; and optionally irradiating the biological sample; or
        (3) washing the biological sample using a buffered aqueous solution to remove the hematoxylin and partially remove the eosin; contacting the biological sample with an electron transfer reagent; and irradiating the biological sample to remove residual fluorescence.

2. The method of claim 1, wherein removing the fluorescent hematoxylin and eosin signals from the biological sample includes a wash using a buffered aqueous solution.

3. The method of claim 1, wherein removing the fluorescent hematoxylin and eosin signals from the biological sample comprises
(i) washing the biological sample using a buffered aqueous solution to remove the hematoxylin and partially remove the eosin; and
(ii) contacting the biological sample with a charge transfer reagent to quench the residual fluorescence.

4. The method of claim 1, wherein removing the fluorescent hematoxylin and eosin signals from the biological sample comprises
(i) washing the biological sample using a buffered aqueous solution to remove the hematoxylin and partially remove the eosin;
(ii) contacting the biological sample with hydrogen peroxide and a metal salt to generate hydroxyl radicals; and
(iii) optionally irradiating the biological sample.

5. The method of claim 1, wherein removing the fluorescent hematoxylin and eosin signals from the biological sample comprises
(i) washing the biological sample using a buffered aqueous solution to remove the hematoxylin and partially remove the eosin;
(ii) contacting the biological sample with an electron transfer reagent; and
(iii) irradiating the biological sample to remove residual fluorescence.

6. The method of claim 5, wherein irradiating the biological sample is accomplished by exposing the biological sample to light of 350 nm-1.3 μM in wavelength.

7. The method of claim 6, wherein irradiating the biological sample is accomplished by exposing the biological sample to light of 400-700 nm in wavelength.

8. The method of claim 5, wherein irradiating the biological sample is carried out in the presence of a buffer at pH of 5-9.

9. The method of claim 5, wherein irradiating the biological sample is carried out at a temperature of 4-50° C.

10. The method of claim 5, wherein irradiating the biological sample is performed for about 20 seconds to about 15 minutes.

11. The method of claim 5, wherein the eosin is irreversibly modified.

12. The method of claim 5, wherein no detectable signal is detected after biological sample irradiation.

13. The method according to claim 5, wherein the electron transfer reagent is a borate salt.

14. The method of claim 13, wherein the borate salt is represented by the following structural formula:

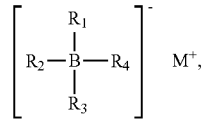

wherein:
each $R_1$, $R_2$, and $R_3$ is, independently, an alkyl, an alkenyl, an akynyl, an aryl or a heteroaryl, wherein said alkyl, alkenyl, alkynyl, aryl or heteroaryl is optionally substituted with one or more substituents selected from the group consisting of (C1-C4)alkyl, (C1-C4)alkoxy, (C1-C4)alkylamino, amino, hydroxyl, cyano, halogen, or nitro,
$R_4$ is an alkyl, an alkenyl, or an akynyl, wherein said alkyl, alkenyl, or alkynyl is optionally substituted with one or more substituents selected from the group consisting of (C1-C4)alkyl, aryl, (C1-C4) alkoxy, (C1-C4)alkylamino, amino, hydroxyl, cyano, halogen, or nitro, and
$M^+$ is selected from the group consisting of organic and inorganic cations.

15. The method of claim 14, wherein each of $R_1$, $R_2$, and $R_3$ is each independently an optionally substituted aryl and $R_4$ is an optionally substituted alkyl.

16. The method of claim 15, wherein each of $R_1$, $R_2$, and $R_3$ is phenyl and $R_4$ is butyl, or benzyl.

17. The method of claim 14, wherein $M^+$ is an inorganic cation selected from the group consisting of $Li^+$, $Na^+$, and $K^+$.

18. The method of claim 1, wherein detecting additional features or targets in the biological sample comprises:
(i) binding at least one probe to one or more targets of the biological sample;
(ii) detecting a signal from the at least one bound probe; and
(iii) optionally removing the signal and optionally repeating steps (i) through (iii).

19. The method of claim 18, wherein removing the signal in step (iii) three includes exposure to a photoactivated chemical bleaching agent and irradiating the biological sample by exposing the sample to light of 350 nm-1.3 μM in wavelength.

20. The method of claim 18, wherein the at least one probe in step (i) comprises a fluorescent signal generator, and the signal detected in step (ii) is a fluorescent signal.

21. The method of claim 18, wherein removing the signal in step (iii) comprises contacting the biological sample with a bleaching or stripping agent or subjecting the biological sample to heat to remove the probe or a signal thereof.

22. The method of claim 21, wherein the stripping agent is SDS and the probe is an antibody.

23. The method of claim 21, wherein the probe is stripped by direct heat or microwave induced heat in the presence of a buffer.

24. The method of claim 18, wherein removing the signal includes adding a charge transfer reagent to the biological sample, before step (ii), to quench residual fluorescence.

25. A method of probing multiple targets in a biological sample, comprising:
(a) optionally detecting hematoxylin and eosin staining of a biological sample containing multiple targets and stained with hematoxylin and eosin;
(b) optionally removing the hematoxylin and partially removing the eosin by washing the biological sample;
(c) subjecting the biological sample to an antigen retrieval process to expose one or more antigens in a region of interest;
(d) optionally applying a blocking reagent to block against nonspecific binding of one or more antigens;
(e) removing fluorescent hematoxylin and eosin signals from the biological sample;
(f) binding at least one probe to one or more targets present in the biological sample;
(g) detecting a signal from the at least one bound probe; and
(h) optionally removing the signal and optionally repeating steps (f) through (h);

wherein removing the fluorescent hematoxylin and eosin signals from the biological sample comprises:
  (1) washing the biological sample using a buffered aqueous solution to remove the hematoxylin and partially remove the eosin; and contacting the biological sample with a charge transfer reagent to quench residual fluorescence;
  (2) washing the biological sample using a buffered aqueous solution to remove the hematoxylin and partially remove the eosin; contacting the biological sample with hydrogen peroxide and a metal salt to generate hydroxyl radicals; and optionally irradiating the biological sample; or
  (3) washing the biological sample using a buffered aqueous solution to remove the hematoxylin and partially remove the eosin; contacting the biological sample with an electron transfer reagent; and irradiating the biological sample to remove residual fluorescence.

26. The method of claim 25, wherein removing the signal in step (h) comprises contacting the biological sample with a bleaching agent or stripping agent or subjecting the biological sample to heat to remove the at least one probe or a signal thereof.

27. The method of claim 25, wherein said at least one probe is a protein binder.

28. A method of probing multiple targets in a biological sample, comprising:
  (a) optionally detecting hematoxylin and eosin staining in a biological sample containing multiple targets and stained with hematoxylin and eosin;
  (b) removing fluorescent hematoxylin and eosin signals from the biological sample;
  (c) binding at least one probe to one or more targets present in the biological sample;
  (d) detecting a signal from the at least one bound probe; and
  (e) optionally removing the signal and optionally repeating steps (c) through (e);
wherein removing the fluorescent hematoxylin and eosin signals from the biological sample comprises:
  (1) washing the biological sample using a buffered aqueous solution to remove the hematoxylin and partially remove the eosin; and contacting the biological sample with a charge transfer reagent to quench residual fluorescence;
  (2) washing the biological sample using a buffered aqueous solution to remove the hematoxylin and partially remove the eosin; contacting the biological sample with hydrogen peroxide and a metal salt to generate hydroxyl radicals; and optionally irradiating the biological sample; or
  (3) washing the biological sample using a buffered aqueous solution to remove the hematoxylin and partially remove the eosin; contacting the biological sample with an electron transfer reagent; and irradiating the biological sample to remove residual fluorescence.

29. The method of claim 28, wherein removing the signal in step (e) comprises subjecting the biological sample to at least one of a bleaching agent, a protein denaturant, a DNA denaturant, heat, or SDS.

30. The method according to claim 28, wherein the at least one probe is a FISH probe.

* * * * *